(12) United States Patent
Wu et al.

(10) Patent No.: US 12,409,213 B2
(45) Date of Patent: Sep. 9, 2025

(54) LIVE ATTENUATED ORAL VACCINE AGAINST SHIGELLOSIS AND TYPHOID FEVER

(71) Applicant: Sanaria Inc., Rockville, MD (US)

(72) Inventors: Yun Wu, Rockville, MD (US); Dennis J. Kopecko, Silver Spring, MD (US); B. Kim Lee Sim, Gaithersburg, MD (US); Stephen L. Hoffman, Gaithersburg, MD (US)

(73) Assignee: Sanaria Inc., Rockville, MD (US)

( * ) Notice: Subject to any disclaimer, the term of this patent is extended or adjusted under 35 U.S.C. 154(b) by 430 days.

(21) Appl. No.: 17/660,558

(22) Filed: Apr. 25, 2022

(65) Prior Publication Data

US 2022/0323562 A1     Oct. 13, 2022

Related U.S. Application Data

(62) Division of application No. 16/897,999, filed on Jun. 10, 2020, now Pat. No. 11,324,814, which is a division of application No. 15/742,459, filed as application No. PCT/US2016/041192 on Jul. 6, 2016, now Pat. No. 10,695,415.

(60) Provisional application No. 62/189,083, filed on Jul. 6, 2015.

(51) Int. Cl.
| | | |
|---|---|---|
| *A61K 39/112* | (2006.01) | |
| *A61K 39/00* | (2006.01) | |
| *A61K 39/116* | (2006.01) | |

(52) U.S. Cl.
CPC ...... *A61K 39/0283* (2013.01); *A61K 39/0275* (2013.01); *A61K 39/116* (2013.01); *A61K 2039/522* (2013.01); *A61K 2039/523* (2013.01); *A61K 2039/543* (2013.01); *A61K 2039/70* (2013.01); *Y02A 50/30* (2018.01)

(58) Field of Classification Search
CPC ............ A61K 39/0283; A61K 39/0275; A61K 39/116; A61K 2039/541; A61K 2039/542
See application file for complete search history.

(56) References Cited

U.S. PATENT DOCUMENTS

| | | |
|---|---|---|
| 7,541,043 B2 | 6/2009 | Kopecko et al. |
| 8,071,084 B2 | 12/2011 | Kopecko et al. |
| 8,119,365 B2 | 2/2012 | Blattner et al. |
| 8,337,832 B2 | 12/2012 | Kopecko et al. |
| 8,992,943 B2 | 3/2015 | Kopecko et al. |
| 9,284,566 B2 | 3/2016 | Liao et al. |
| 9,580,718 B2 | 2/2017 | Curtiss et al. |
| 10,695,415 B2 | 6/2020 | Yun et al. |
| 11,324,814 B2 | 5/2022 | Yun et al. |
| 2005/0281841 A1 | 12/2005 | Kopecko et al. |
| 2007/0054358 A1 | 3/2007 | Blattner et al. |
| 2013/0288325 A1 | 10/2013 | Liao et al. |
| 2018/0264099 A1 | 9/2018 | Yun et al. |
| 2020/0376107 A1 | 12/2020 | Yun et al. |

FOREIGN PATENT DOCUMENTS

| | | | |
|---|---|---|---|
| WO | WO 2014/043637 | * | 3/2014 |
| WO | WO-2014043637 A1 | | 3/2014 |
| WO | WO-2015021147 A1 | | 2/2015 |

OTHER PUBLICATIONS

Hoppner, Horm Re. 2002, 58 Suppl. 3:7-15 (Year: 2002).*
Lodish et al., Mol. Cell Biol., 3rd ed. Scientific American Books, NY, 1995) (Year: 1995).*
Bryce, J., et al., "WHO estimates of the causes of death in children," *Lancet* 365(9465):1147-1152, Elsevier, Netherlands (Mar. 2005).
Bardhan, P., et al., "Decrease in shigellosis-related deaths without *Shigella* spp.-specific interventions, Asia," *Emerging Infectious Diseases* 16(11):1718-23, Centers for Disease Control and Prevention, United States (Nov. 2010).
Livio, S., et al., "*Shigella* Isolates From the Global Enteric Multicenter Study Inform Vaccine Development," *Clin Infect Dis* 59(7):933-941, Oxford University Press on behalf of the Infectious Diseases Society of America, Untied States (Oct. 2014).
Scallan, E., et al., "Foodborne illness acquired in the United States*—major pathogens," *Emerg Infect Dis* 17(1):7-15, Centers for Disease Control and Prevention, United States (Jan. 2011).
Bowen, A, et al., "Notes from the Field: Outbreaks of *Shigella sonnei* Infection with Decreased Susceptibility to Azithromycin Among Men Who Have Sex with Men—Chicago and Metropolitan Minneapolis-St. Paul, 2014," *AlMWRMorb Mortal Wkly Rep* 64(21):597-598 (Jun. 2015).
Howie, R.L., et al., "Reduced azithromycin susceptibility in *Shigella sonnei*, United States," *Microb Drug Resist* 16(4): 245-248, Mary Ann Liebert, United States (Dec. 2010).
Karlsson, M. S., et al., "Outbreak of infections caused by *Shigella sonnei* with reduced susceptibility to azithromycin in the United States," *Antimicrob Agents and Chemother* 57(3): 1559-1560, American Society for Microbiology, United States (Mar. 2013).
Gu, B., et al., "Comparison of the prevalence and changing resistance to nalidixic acid and ciprofloxacin of *Shigella* between Europe-America and Asia-Africa from 1998 to 2009," *Int J Antimicrob Agents* 40(1): 9-17, Elsevier, Netherlands (Apr. 2012).

(Continued)

*Primary Examiner* — Brian Gangle
*Assistant Examiner* — Lakia J Jackson-Tongue
(74) *Attorney, Agent, or Firm* — Sterne, Kessler, Goldstein &Fox P.L.L.C.

(57) ABSTRACT

Disclosed is the attenuated *Salmonella typhi* vaccine Ty21a utilized as a vector for *Shigella* and/or enterotoxigenic *E. coli* genes stably integrated in the Ty21a chromosome. These genes include a heterologous *Shigella sonnei* O-antigen biosynthetic gene region that comprises the wzz gene and expresses *Shigella sonnei* form 1 O-antigen, as well as a heterologous acid resistance biosynthetic gene system comprising a YbaS gene, which enables increased stability of the Ty21a vector at pH 2.5 relative to Ty21a without the integrated acid resistance biosynthetic gene system.

Figures 4A, 4B, 4C:
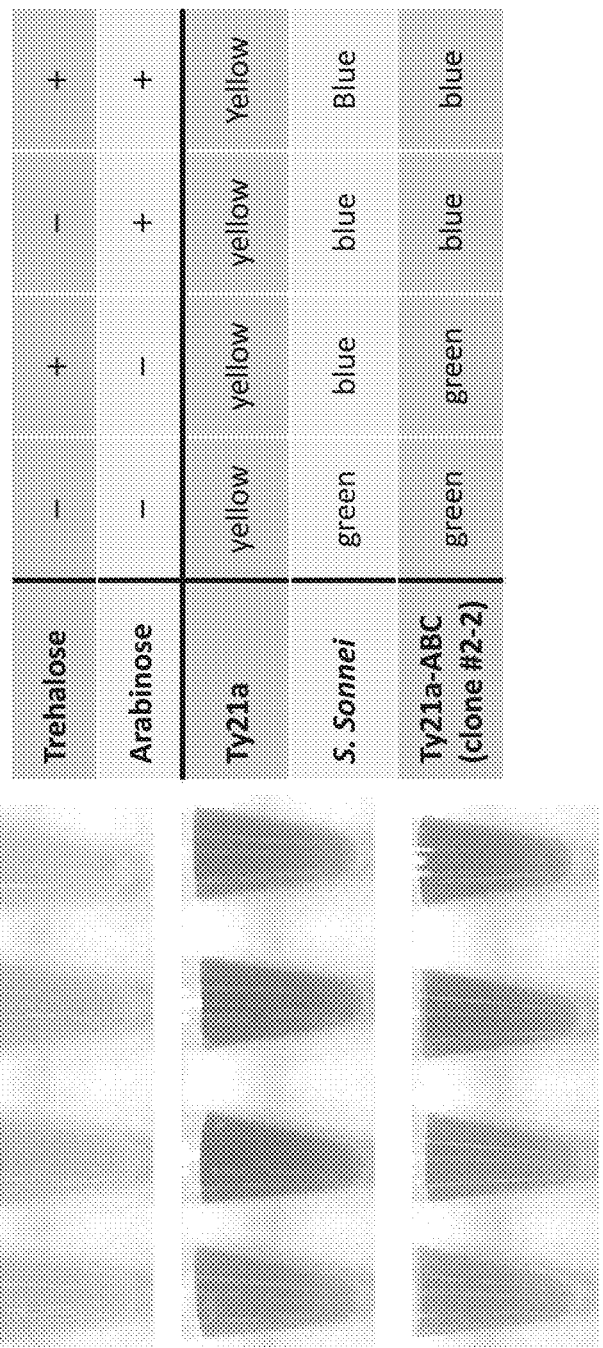

11 Claims, 14 Drawing Sheets
Specification includes a Sequence Listing.

(56) References Cited

OTHER PUBLICATIONS

Robbins, J.B., et al., "Hypothesis for vaccine development: protective immunity to enteric diseases caused by nontyphoidal salmonellae and shigellae may be conferred by serum IgG antibodies to the O-specific polysaccharide of their lipopolysaccharides," *Clin Infect Dis* 15(2): 346-361, Oxford University Press on behalf of the Infectious Diseases Society of America, Untied States (Aug. 1992).
Kopecko, D.J., et al., "Genetic stability of vaccine strain *Salmonella* Typhi Ty21a over 25 years," *Int J Med Microbiol* 299(4): 233-246, Elsevier, Netherlands (Jan. 2009).
Levine, M.M., Typhoid fever vaccines, in Vaccines, S.A. Plotkin and W.A. Orenstein, Editors., W.B. Saunders: Philadelphia. 781-814 (1999).
Levine, M.M., et al., "Duration of efficacy of Ty21a, attenuated *Salmonella typhi* live oral vaccine," *Vaccine* 17 Suppl2: S22-7, Elsevier, United States (Oct. 1999).
Wahdan, M.H., et al., "A controlled field trial of live *Salmonella typhi* strain Ty 21a oral vaccine against typhoid: three-year results," *J Infect Dis* 145(3): 292-5, Oxford University Press on behalf of the Infectious Diseases Society of America, United States (Mar. 1982).
Gilman, R.H., et al., "Evaluation of a UDP-glucose-4-epimeraseless mutant of *Salmonella typhi* as a liver oral vaccine," *J Infect Dis* 136(6):717-23, Oxford University Press on behalf of the Infectious Diseases Society of America, United States (Dec. 1977).
Cryz, SJ., Jr., "Post-marketing experience with live oral Ty21a vaccine," *Lancet* 341(8836): 49-50, Elsevier, Netherlands (Jan. 1993).
Simanjuntak, C.H., et al., "Oral immunisation against typhoid fever in Indonesia with Ty21a vaccine," *Lancet* 338(8774): 1055-1059, Elsevier, Netherlands (Oct. 1991).
Levine, M.M., et al., "The efficacy of attenuated *Salmonella typhi* oral vaccine strain TY21A evaluated in controlled field trials, " Development of vaccines and drugs against diarrhea: 11th Nobel Conference, Stockholm, 1985, in 11th Noble Conference, J. Holmgren, A. Lindberg, and R Mollby, Editors, Studentlitteratur, Lund, Sweden. Stockholm. 90-101 (1986).
Ohtake, S., et al., "Room temperature stabilization of oral, live attenuated *Salmonella enterica* serovar Typhi-vectored vaccines," *Vaccine* 29(15): 2761-2771, Elsevier, United States (Feb. 2011).
Dharmasena, M.N., et al., "Stable expression of *Shigella sonnei* form I O-polysaccharide genes recombineered into the chromosome of live *Salmonella* oral vaccine vector Ty21a," *Int J Med Microbial* 303(3): 105-113, Elsevier, Netherlands (Mar. 2013).
Pickett, T.E., et al., "In vivo characterization of the murine intranasal model for assessing the immunogenicity of attenuated *Salmonella enterica* serovar Typhi strains as live mucosal vaccines and as live vectors," *Infect Immun* 68(1):205-213, American Society for Microbiology, United States (Jan. 2000).
Lin, J., et al., "Comparative analysis of extreme acid survival in *Salmonella typhimurium, Shigella flexneri*, and *Escherichia coli," J Bacteriol* 177(14):4097-4104, American Society for Microbiology, United States (Jul. 1995).
Gorden, J., et al., "Acid resistance in enteric bacteria," *Infect Immun* 61(1):364-367, American Society for Microbiology, United States (Jan. 1993).
Audia, J.P., et al., "Breaking through the acid barrier: an orchestrated response to proton stress by enteric bacteria," *Int J Med Microbial* 291(2):97-106 (May 2001).
Foster, J.W., "*Salmonella* acid shock proteins are required for the adaptive acid tolerance response," *J Bacteriol* 173(21): 6896-6902, American Society for Microbiology, United States (Nov. 1991).
Foster, J.W., "The acid tolerance response of *Salmonella typhimurium* involves transient synthesis of key acid shock proteins," *J Bacteriol* 175(7): 1981-1987, American Society for Microbiology, United States (Apr. 1993).
Foster, J.W., "Low pH adaptation and the acid tolerance response of *Salmonella typhimurium,"Crit Rev Microbiol* 21(4):215-237 (1995).

Robbe-Saule, V. and F. Norel, "The rpoS mutant allele of *Salmonella typhi* Ty2 is identical to that of the live typhoid vaccine Ty2la," *FEMS Microbial Lett* 170(1): 141-143, Oxford University Press, United Kingdom (Jan. 1999).
Germanier, R. and E. Fuer, "Isolation and characterization of Gal E mutant Ty 21a of *Salmonella typhi*: a candidate strain for a live, oral typhoid vaccine," *J Infect Dis* 131(5): 553-558, Oxford University Press on behalf of the Infectious Diseases Society of America, United States (May 1975).
Hone, D.M., et al., "Adaptive acid tolerance response by *Salmonella typhi* and candidate live oral typhoid vaccine strains," *Vaccine* 12(10):895-898, Elsevier, United States (Aug. 1994).
Kantele, A, et al., "Comparison of the human immune response to live oral, killed oral or killed parenteral *Salmonella typhi* TY21A vaccines," *Microb Pathog* 10(2): 117-26, Academic Press, United States (Feb. 1991).
Waterman, S.R. and P.L. Small, "Identification of the promoter regions and sigma(s) dependent regulation of the gadA and gadBC genes associated with glutamate- dependent acid resistance in *Shigella flexneri," FEMS Microbial Lett* 225(1):155-160, Oxford University Press, United Kingdom (Aug. 2003).
Bhagwat, A.A and M. Bhagwat, "Comparative analysis of transcriptional regulatory elements of glutamate-dependent acid-resistance systems of *Shigella flexneri* and *Escherichia coli* 0157:H7," *FEMS Microbial Lett* 234(1): 139-147, Oxford University Press, United Kingdom (May 2004).
Lin, J., et al., "Mechanisms of acid resistance in enterohemorrhagic *Escherichia coli,"Appl Environ Microbiol* 62(9): 3094-3100, American Society for Microbiology, United States (Sep. 1996).
Brenneman, K.E., et al., "Low-pH rescue of acid-sensitive *Salmonella enterica* Serovar Typhi Strains by a Rhamnose-regulated arginine decarboxylase system," *J Bacteriol* 195(13):3062-3072, American Society for Microbiology, United States (May 2013).
De Biase, D. and E. Pennacchietti, "Glutamate decarboxylase-dependent acid resistance in orally acquired bacteria: function, distribution and biomedical implications of the gadBC operon," *Mal Microbiol* 86(4): 770-786, Malaysian Society for Microbiology, Malaysia (Sep. 2012).
Merrell, D.S. and A Camilli, "Acid tolerance of gastrointestinal pathogens," *Curr Opin Microbiol* 5(1):51-55, Elsevier, Netherlands (Feb. 2002).
Zhao, B. and W.A. Houry, "Acid stress response in enteropathogenic gammaproteobacteria: an aptitude for survival," *Biochem Cell Biol* 88(2):301-31, Canadian Science Publishing, Canada (Apr. 2010).
Hersh, B.M., et al., "A glutamate-dependent acid resistance gene in *Escherichia coli," J Bacteriol* 1 78(13):3978-3981, American Society for Microbiology, United States (Jul. 1996).
Smith, D.K., et al., "*Escherichia coli* has two homologous glutamate decarboxylase genes that map to distinct loci," *J Bacteriol* 174(18): 5820-5826, American Society for Microbiology, United States (Sep. 1992).
Lu, P., et al., "L-glutamine provides acid resistance for *Escherichia coli* through enzymatic release of ammonia," *Cell Res* 23(5): 635-644, Nature Publishing Group on behalf of the Shanghai Institutes for Biological Sciences, China (Jan. 2013).
Ma, D., et al., "Structure and mechanism of a glutamate-GABA antiporter," *Nature* 483(7391):632-636, Springer Nature, Germany (Mar. 2012).
Kopecko, D.J., et al., "Genetic and physical evidence for plasmid control of *Shigella sonnei* form I cell surface antigen," *Infect Immun* 29(1):207-214, American Society for Microbiology, United States (Jul. 1980).
Datsenko, K.A. and B.L. Wanner, "One-step inactivation of chromosomal genes in *Escherichia coli* K-12 using PCR products," *Proc Natl Acad Sci USA* 97(12):6640-6645, National Academy of Sciences, United States (Jun. 2000).
Cherepanov, P. P. and W. Wackernagel, "Gene disruption in *Escherichia coli*: TcR and KmR cassettes with the option of Flp-catalyzed excision of the antibiotic-resistance determinant," *Gene* 158(1): 9-14, Elsevier, Netherlands (May 1995).

(56) References Cited

OTHER PUBLICATIONS

Rice, E.W., et al., "Rapid glutamate decarboxylase assay for detection of *Escherichia coli*," *Appl Environ Microbiol* 59(12): 4347-4349, American Society for Microbiology, United States (Dec. 1993).

Xu, D.Q., et al., "Molecular cloning and characterization of genes for *Shigella sonnei* form IO polysaccharide: proposed biosynthetic pathway and stable expression in a live *Salmonella* vaccine vector," *Infect Immun* 70(8): 4414-4423, American Society for Microbiology, United States (Aug. 2002).

Shepherd, J. G., et al., "Comparison of O-antigen gene clusters of *Escherichia coli* (*Shigella*) sonnei and *Plesiomonas shigellojdes* O17: sonnei gained its current plasmid-borne O-antigen genes from *P. shigelloides* in a recent event," *Infect Immun* 68(10): 6056-6061, American Society for Microbiology, United States (Oct. 2000).

Vivotif [package insert—USA]. Crucell Switzerland LTD; Sep. 2013, accessed at https://wayback.archiveit.org/7993/20170406143500/https://www.fda.gov/downloads/BiologicsBloodVaccines/Vaccines/ApprovedProducts/UCM 142807.pdf.

Batzer, M.A., et al., "Enhanced evolutionary PCR using oligonucleotides with inosine at the 3'-terminus," *Nucleic Acid Res* 19(18):5081, Oxford University Press, United Kingdom (Sep. 1991).

Karlin, S. and S.F. Altschul, "Applications and statistics for multiple high-scoring segments in molecular sequences," *Proc Natl Acad Sci USA* 90(12):5873-5877, National Academy of Sciences, United States (Jun. 1993).

Ohtsuka, E., et al., "An alternative approach to deoxyoligonucleotides as hybridization probes by insertion of deoxyinosine at ambiguous codon positions," *J Biol Chem* 260(5):2605-2608, American Society for Biochemistry and Molecular Biology, United States (Mar. 1985).

Rossolini, G.M., et al., "Use of deoxyinosine-containing primers vs degenerate primers for polymerase chain reaction based on ambiguous sequence information," *Mol Cell Probes* 8(2):91-98, Elsevier, Netherlands (Apr. 1994).

National Enteric Disease Surveillance: Shigella Annual Report, 2012, "Human surveillance Data: Laboratory-based Enteric Disease Surveillance (LEDS)," accessed at http://www.cdc.gov/ncezid/dfwed/PDFs/shigella-annual -report-2012-508c.pdf accessed on Apr. 2014, 9 pages.

International Search Report and Written Opinion for International Application No. PCT/US2016/041192, United States Patent Office, United States, mailed Oct. 4, 2016, 10 pages.

Dharmasena, M.N., et al., "Development of an Acid-Resistant Salmonella Typhi Ty2la Attenuated Vector For Improvement Oral Vaccine Delivery," *PLOS One*: e01635 11, Public Library of Science, United States (Sep. 2016).

Lu, P., et al., "Supplementary information; L-glutamine provides acid resistance for *Escherichia coli* through enzymatic release of ammonia," *Cell Research* 23(5): 1-11, Nature Publishing Group, United Kingdom (Jan. 2013).

Lund, P., et al., "Coping with low pH: molecular strategies in neutralophilic bacteria," *FEMS Microbiology Reviews* 38(6): 1091-1125, Oxford Academic, United Kingdom (Jul. 2014).

Martinic, M., et al., "Contribution of the Lipopolysaccharide to Resistance of Shingella flexneri 2a to Extreme Acidity," *PLOS One* 6(1):e25557, Public Library of Science United States (Oct. 2011).

Lodish, H., "Nucleic Acid Polymerization Can be Described By Four Rules," Nucleic Acid Synthesis, Molecular Biology of the Cell 3ed, 3 pages, Scientific American Books, United States (1995).

Hoppner W., et al., "Clinical Impact of Molecular Diagnostics in Endocrinology: Polymorphism, Mutations and DNA technologies," *Hormone Research* 58(3):7-15, Karger, Germany (2002).

Wai, T., et al., "Multi-valent Oral Vaccine Against Enterotoxigenic *Escherichia coli* (ETEC) & Enteric Fevers," Presented at the American Society of Tropical Medicine & Hygiene (ASTMH) 68th Annual Meeting, in National Harbor, MD, United States, 1 page (Nov. 2019).

* cited by examiner

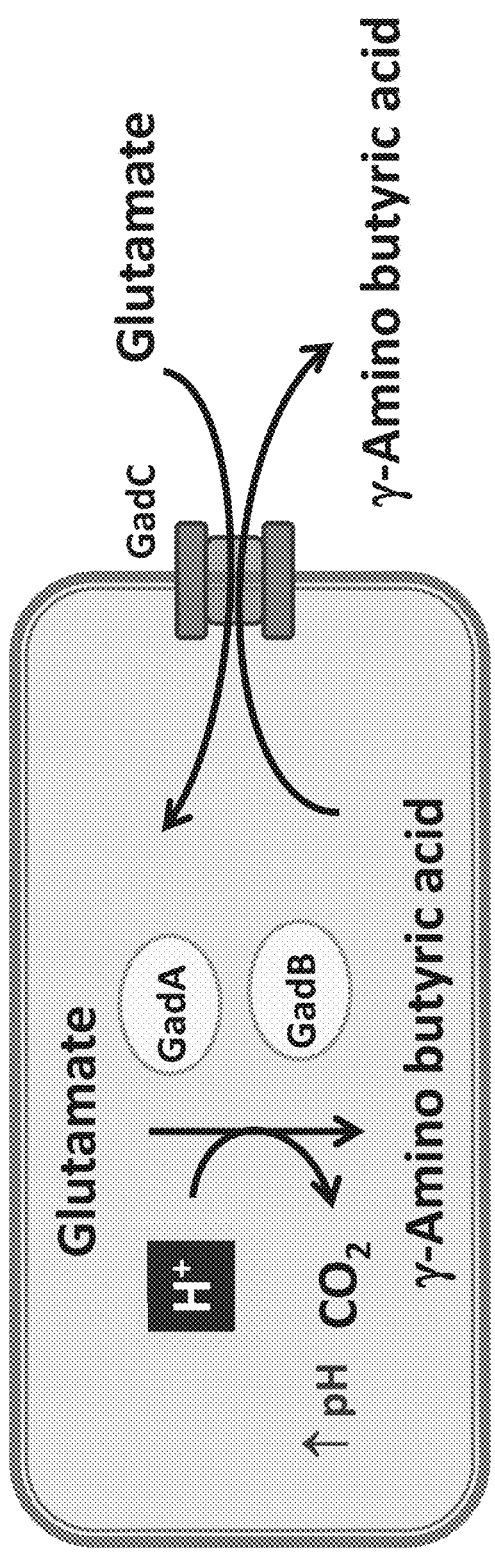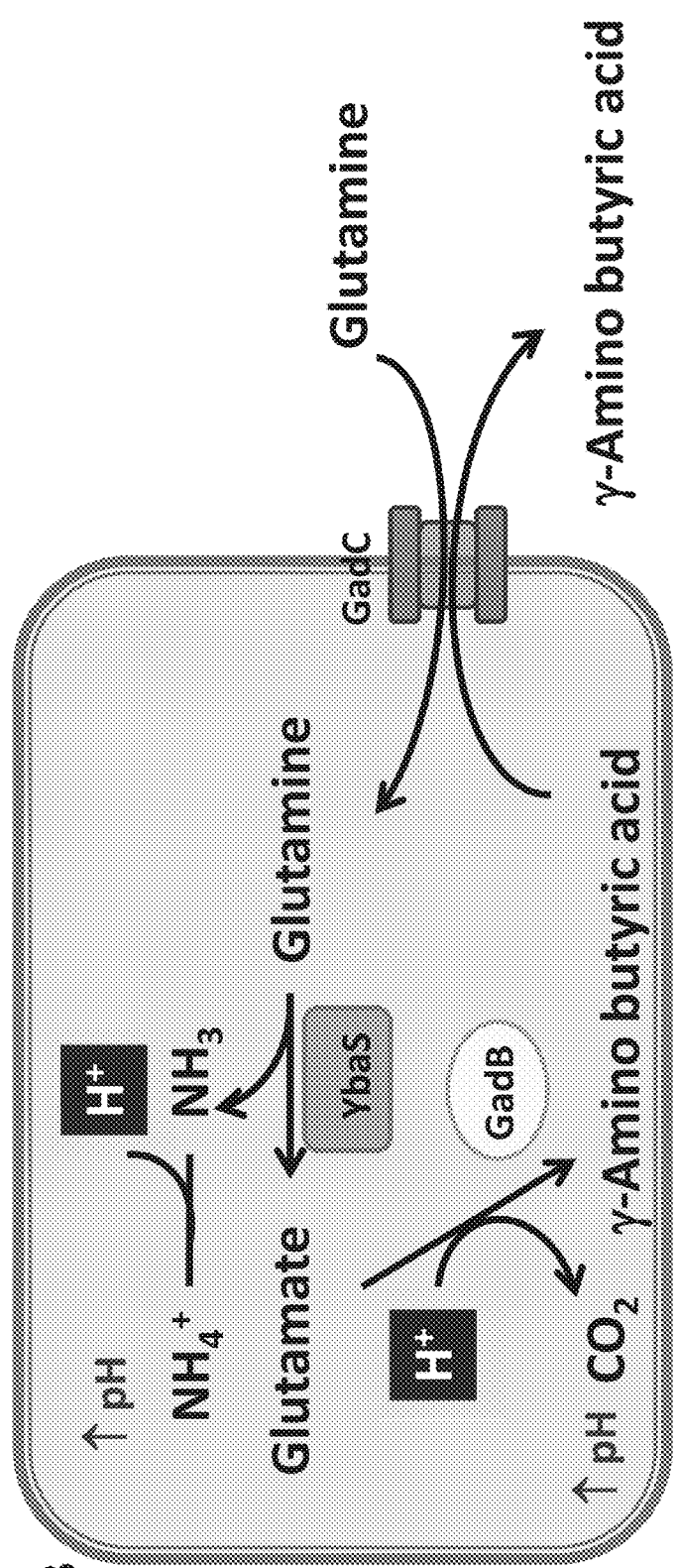
FIG. 1A
FIG. 1B

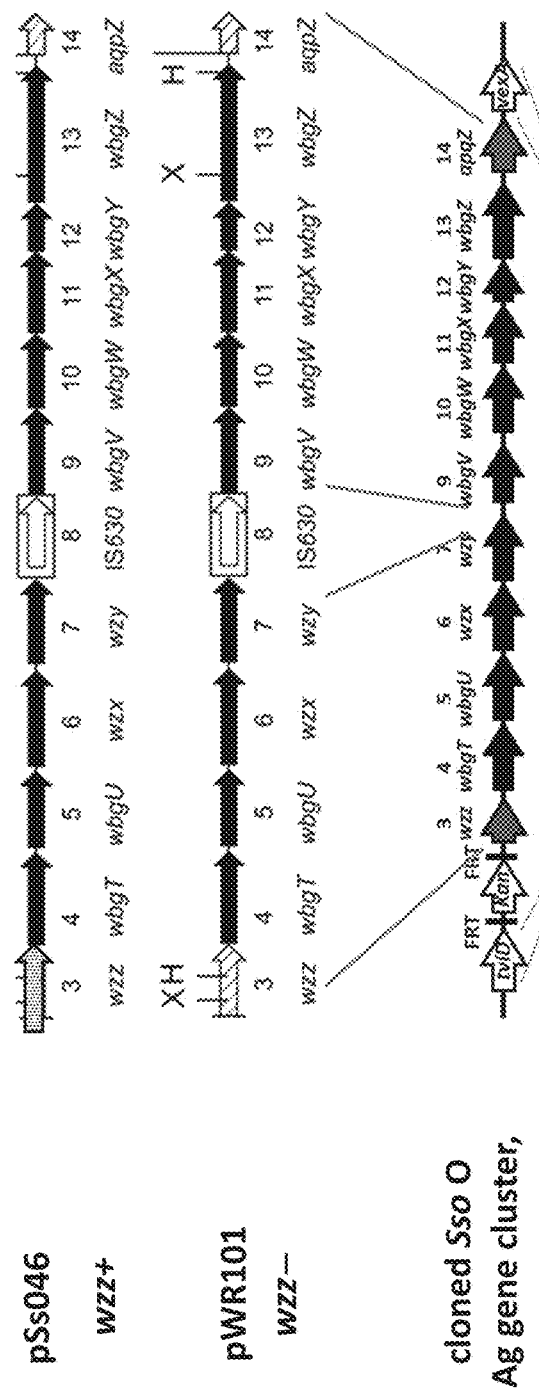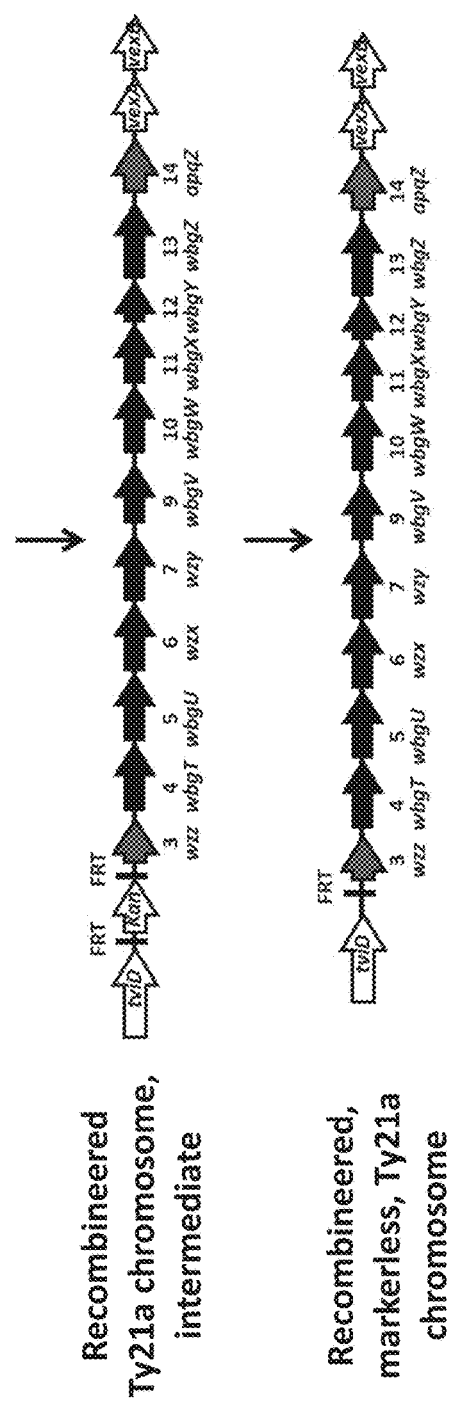

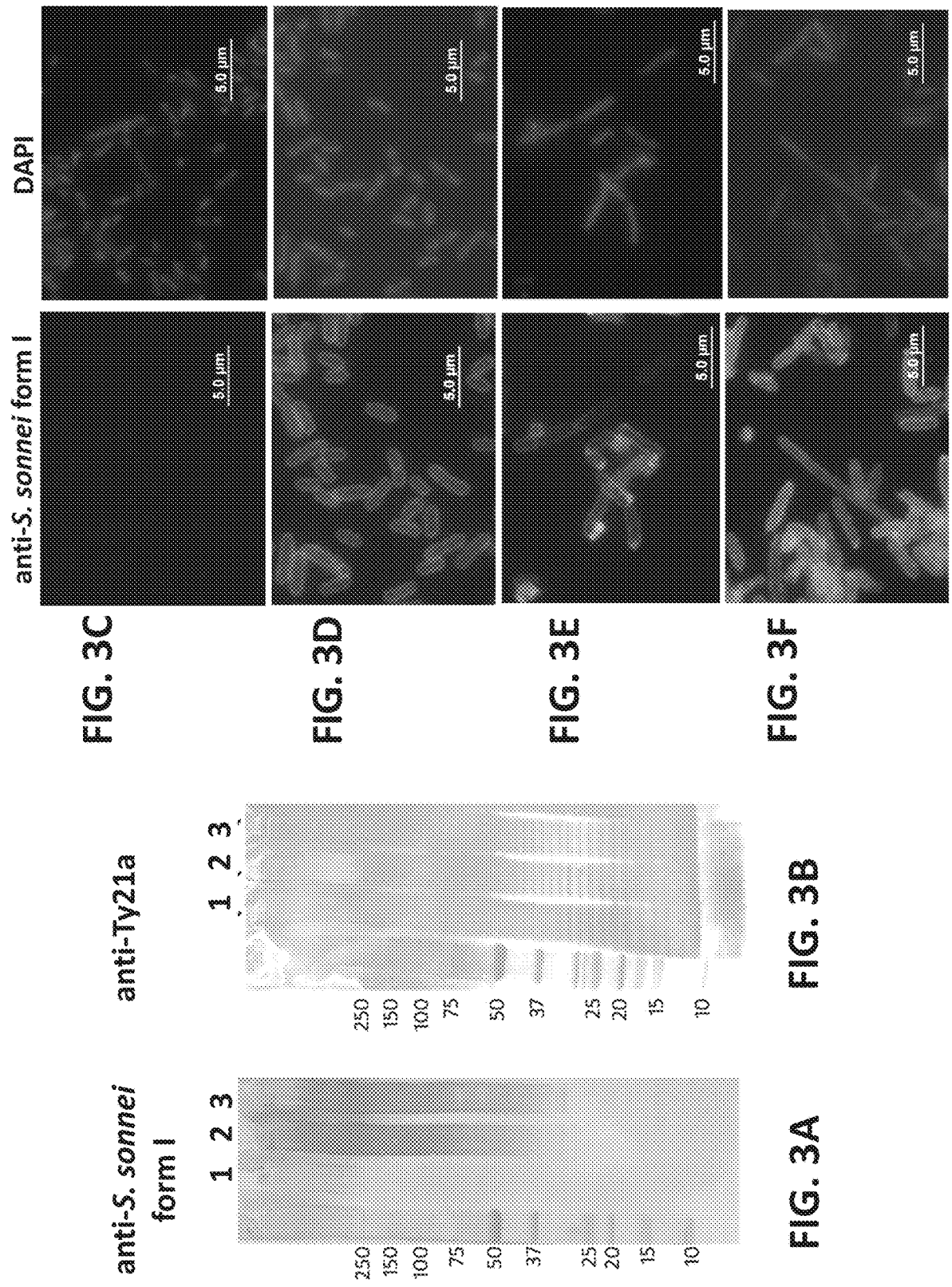

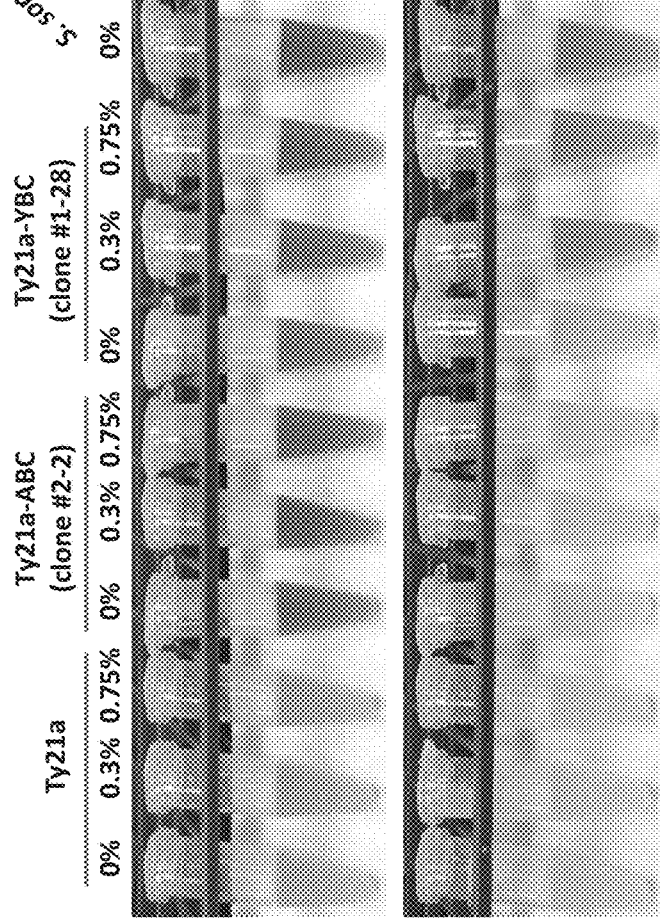

LIVE ATTENUATED ORAL VACCINE AGAINST SHIGELLOSIS AND TYPHOID FEVER

CROSS REFERENCE TO RELATED APPLICATIONS

This application is a divisional application of U.S. application Ser. No. 16/897,999, filed Jun. 10, 2020, currently allowed, which is a divisional application of U.S. application Ser. No. 15/742,459, filed Jan. 5, 2018, now U.S. Pat. No. 10,695,415, which is a U.S. national stage application of International Appl. No. PCT/US2016/041192, filed Jul. 6, 2016, which claims the priority benefit of U.S. Provisional Appl. No. 62/189,083, filed Jul. 6, 2015, each of which is hereby incorporated by reference in its entirety.

STATEMENT OF GOVERNMENT INTEREST

This invention was made with government support under SBIR grant R43AI106158, "Live Attenuated Oral Typhoid-Shigellosis Vaccine," awarded by the National Institute of Health. The government has certain rights in the invention. All strains disclosed herein were constructed without government support. However, characterization of strains was supported in part by SBIR grant R43AI106158, "Live Attenuated Oral Typhoid-Shigellosis Vaccine".

REFERENCE TO A SEQUENCE LISTING

The instant application contains a Sequence Listing, which is submitted in ASCII format via EFS-Web and is hereby incorporated by reference in its entirety. This ASCII copy, created on Apr. 5, 2022, is named "4661 0160003_SequenceListing_ST25.txt" and is 37,461,448 bytes in size, and was originally submitted in International Appl. No. PCT/US2016/041192.

BACKGROUND OF THE INVENTION

Recent retrospective analyses indicate that the global burden of *Shigella* infections is >125 million annually [1,2]. Shigellosis affects mainly children and causes at least 250,000 deaths per year. There are more than 40 serotypes of *Shigella*, but only a few are responsible for the majority of shigellosis. In developing countries, S. flexineri accounts for most of the case isolates in children under age 5, while *S. sonnei* is the second leading causative species, at about 24% [3]. In developed countries, *S. sonnei* is the leading cause of shigellosis. In United States alone, CDC estimates that there are about 500,000 cases every year; of which 75% are caused by *S. sonnei*. (reviewed in [4] and CDC, National Enteric Disease Surveillance: *Shigella* Annual Report, 2012 worldwideweb.cdc.gov/ncezid/dfwed/PDFs/*shigella*-annual-report-2012-508c.pdf).

In recent years, incidents of drug-resistant *S. sonnei* infection associated with international travellers and adult males who have sex with men have been increasingly reported [5-8]. *Shigella* is listed by both NIAID and DOD as a high priority pathogen.

Vaccines comprise a rational and cost-effective means for protecting against infectious diseases. Protection against shigellosis is believed to be based mainly on anti-O polysaccharide (or O antigen) antibodies [9].

*Salmonella Typhi* Ty21a typhoid vaccine (Vivotif®) [10] is the only live, oral, attenuated bacterial vaccine licensed in the US. Ty21a, when administered for a one week period, affords sustained protection from typhoid fever for 7 years with efficacies ranging from 62-96% as reported in Chilean/Egyptian field trials [11-13], and it has had an unrivaled safety record during the past 25 years [14-17]. There has never been a reported case of bacteremic dissemination of Ty21a after administration to more than 200 million recipients [10], and Ty21a is nonpathogenic even when given at 100 times the standard dose [12]. Also, there are no reports of post-vaccination inflammatory arthritis (e.g., Reiter's syndrome) with Ty21a, a potential problem with other live attenuated vectors including nontyphoid *Salmonella, Shigella*, and *Yersinia*. In addition, Ty21a can be foam-dried, which provides for temperature stabilization and a potential shelf life of 5-10 years [18].

Dr. Kopecko's lab used Ty21a as a vector to express *S. sonnei* form I O-antigen from an expression cassette inserted into plasmids (U.S. Pat. Nos. 7,541,043; 8,071,084; 8,337,832; and 8,992,943). Additionally, a recombinant Ty21a strain carrying a genome-integrated *S. sonnei* form I O-antigen gene cluster constructed in Dr. Kopecko's Lab induced high levels of serum antibodies against both *S. sonnei* form I O-antigen and *Salmonella* O9, 12 O-antigen and protected against lethal challenge of *S. sonnei* in mice [19 and WO2014/04367]. However, the immunization and infection route was by intraperitoneal (IP) injection, which is not the route for Ty21a immunization per se, nor is it the natural *S. Typhi* or *S. sonnei* route of infection. LPS alone immunized through the mucosal route is not immunogenic [20]. Moreover, high serum IgG does not directly reflect the strength of local mucosal immune responses.

Curtiss et al. described a bacterial recombinant comprising a Gad B/C acid resistance cassette [49].

There is a need for bivalent and multivalent transgenic attenuated, acid resistant vaccines for protection against shigellosis and typhoid fever.

SUMMARY OF THE INVENTION

This application is related generally to bioengineering, and to multivalent oral vaccines for protection against shigellosis and typhoid fever.

The present invention relates to the development of a bivalent, oral, live attenuated, acid stable composition (e.g., a vaccine) for use against shigellosis caused by *Shigella sonnei* and typhoid fever caused by *Salmonella enterica* serovar typhi (referred to herein as *S. typhi* or *Salmonella typhi*). Disclosed herein is the characterization of the constructed vaccine strains, e.g., Ty21a-YBC-Sso (clone #34-1) administered through immunization routes, including, e.g., oral administration. This invention discloses the preparation and use of the attenuated *Salmonella enterica* serovar typhi vaccine Ty21a as an expression vector for *Shigella sonnei* genes stably integrated into the Ty21a chromosome. Also disclosed herein is a Ty21a strain co-expressing the concerted YbaS-GadBC AR system and *S. sonnei* form I O antigen and the characterization of such vaccine strain.

In an embodiment, a transgenic *Salmonella typhi* Ty21a is disclosed, comprising a heterologous *Shigella sonnei* O-antigen biosynthetic gene region and further comprising a heterologous acid resistance biosynthetic gene system, said biosynthetic O-antigen gene region and said acid resistance biosynthetic gene system both being integrated into the *Salmonella typhi* Ty21a chromosome, wherein:

a. heterologous *Shigella sonnei* form 1 O-antigen is stably expressed;

b. heterologous *Shigella sonnei* acid resistance enzymes, comprising a YbaS gene, are stably expressed;

c. said transgenic *Salmonella typhi* Ty21a is more stable at pH 2.5 than *Salmonella typhi* Ty21a without the inserted acid resistance biosynthetic gene system;
d. immune response and/or immune protection is elicited against virulent *Shigella sonnei* challenge; and/or
e. immune response and/or immune protection is elicited against virulent *Salmonella typhi* challenge.

In an embodiment, the heterologous *Shigella sonnei* O-antigen biosynthetic gene region of the transgenic Ty21a comprises a wzz gene. In some embodiments, the wzz gene of the invention is derived from the wzz gene having Gene bank accession: NC_007385.1 (193411 . . . 194517). In some embodiments, the wzz gene comprises a DNA sequence that shares at least 90% sequence identity with the DNA sequence of nucleic acids 4,511,904 to 4,513,010 of SEQ ID NO: 4 or a complementary sequence thereof; the DNA sequence of nucleic acids 4,511,904 to 4,513,010 of SEQ ID NO: 4 or a complementary sequence thereof; or a DNA sequence that encodes a functional variant of the polypeptide encoded by the DNA sequence of nucleic acids 4,511,904 to 4,513,010 of SEQ ID NO: 4 or a complementary sequence thereof.

In an embodiment, the heterologous *Shigella sonnei* O-antigen biosynthetic gene region of the transgenic Ty21a comprises a DNA sequence that shares at least 90% sequence identity with the DNA sequence of nucleic acids 4,500,076 to 4,513,461 of SEQ ID NO: 4 or a complementary sequence thereof; the DNA sequence of nucleic acids 4,500,076 to 4,513,461 of SEQ ID NO: 4 or a complementary sequence thereof, or a DNA sequence that encodes a functional variant of the polypeptide encoded by the DNA sequence of nucleic acids 4,500,076 to 4,513,461 of SEQ ID NO: 4 or a complementary sequence thereof.

In an embodiment, the transgenic Ty21a heterologous acid resistance biosynthetic gene system comprises a YbaS gene. In some embodiments, the YbaS gene of the invention is derived from the YbaS gene having Genebank accession: NC_007384 (REGION: 504891 . . . 505823). In some embodiments, the YbaS gene comprises a DNA sequence that shares at least 90% sequence identity with the DNA sequence of nucleic acids 4,503,240 to 4,504,172 of SEQ ID NO: 1 or a complementary sequence thereof, the DNA sequence of nucleic acids 4,503,240 to 4,504,172 of SEQ ID NO: 1 or a complementary sequence thereof; or a DNA sequence that encodes a functional variant of the polypeptide encoded by the DNA sequence of nucleic acids 4,503,240 to 4,504,172 of SEQ ID NO: 1 or a complementary sequence thereof.

In an embodiment, the transgenic Ty21a comprises a nucleic acid insert comprising AraC-YbaS-GadBC-Sso O Ag wzz+. In some embodiments, the AraC-YbaS-GadBC-Sso O Ag wzz+ insert comprises a DNA sequence that shares at least 90% sequence identity with the DNA sequence of nucleic acids 4,500,075-4,518,404 of SEQ ID NO:6 or a complementary sequence thereof; the DNA sequence of nucleic acids 4,500,075-4,518,404 of SEQ ID NO:6 or a complementary sequence thereof, or a DNA sequence that encodes a functional variant of the polypeptide encoded by the DNA sequence of nucleic acids 4,500,075-4,518,404 of SEQ ID NO:6 or a complementary sequence thereof.

In an embodiment, the transgenic Ty21a additionally comprises an O-antigen biosynthetic gene region from a bacterial strain selected from the group consisting of: *Shigella dysenteriae*, *Shigella flexneri*, *Shigella boydii*, *Escherichia coli*, *Salmonela enterica* serovars, *Vibrio cholera* serotypes, *Enterobacter* species, *Yersinia* species, *Pseudomonas* species, and a combination thereof.

Certain embodiments are directed to compositions, e.g., bacterial compositions, comprising a transgenic Ty21a disclosed herein in combination with a carrier that renders the construct suitable for pharmaceutical use.

Certain embodiments are directed to a vaccine suitable for oral administration comprising a transgenic Ty21a disclosed herein in combination with a carrier.

In certain embodiments, administration of a vaccine or composition of the invention to a human population reduces the incidence of shigellosis in that human population subsequently exposed to pathogenic *Shigella sonnei*.

In certain embodiments, administration of a vaccine or composition of the invention to a human population reduces the incidence of typhoid fever in that human population subsequently exposed to pathogenic *S. typhi*.

In certain embodiments, administration of a vaccine or composition of the invention to a human population reduces the incidence of both shigellosis and typhoid fever in that human population subsequently exposed to both pathogenic *Shigella sonnei* and/or pathogenic *S. typhi*.

In certain embodiments, a method of treating, preventing, or reducing the incidence of shigellosis in a human subject is disclosed, e.g., comprising oral administration of one or more doses of a vaccine or composition of the invention.

In certain embodiments, a method of treating, preventing, or reducing the incidence of typhoid fever in a human subject is disclosed, e.g., comprising oral administration of one or more doses of a vaccine or composition of the invention.

In certain embodiments, a method of treating, preventing, or reducing the incidence of both shigellosis and typhoid fever in a human subject is disclosed, e.g., comprising oral administration of one or more doses of a vaccine or composition of the invention.

In some embodiments, the doses are prophylactic.

BRIEF DESCRIPTION OF THE DRAWINGS/FIGURES

FIGS. 1A-1B. Schematic illustration of the glutamate-dependent acid resistant pathway (FIG. 1A) and glutamine-dependent acid resistant pathway (FIG. 1).

FIGS. 2A-2C. Construction of Ty21a-Sso and Ty21a-Sso wzz+. Molecular organizations of the *S. sonnei* form I O antigen gene cluster on pSso046 and pWR101 adapted from [46] (FIG. 2A). Schematic illustration of stable integration of the cloned *S. sonnei* form I O antigen gene cluster, with or without wzz (FIG. 2B), into Ty21a chromosome (FIG. 2C) adapted from [19].

FIGS. 3A-3F. Expression of form I O-antigen in Ty21a-Sso (clone #3-1) and Ty21a-Sso (clone #9-26). LPS was extracted from equivalent amounts of Ty21a (1), Ty21a-Sso (clone #3-1) (2), and Ty21a-Sso (clone #9-26) (3), resolved on a 4-20% Tris-glycine SDS-PAGE gel, transferred to a PVDF membrane, and blotted against rabbit polyclonal antibodies against *S. sonnei* form I (FIG. 3A) or Ty21a (FIG. 3B). Sizes of the molecular weight markers in kDa are indicated to the left of the gel. Fixed bacterial cells were co-stained with rabbit anti-*S. sonnei* form I (left panel), and DNA inside the cells was counter-stained with DAPI (right panel) and visualized by fluorescent microscopy. A representative image is shown for Ty21a (FIG. 3C), *S. sonnei* 53G form I (FIG. 3D), Ty21a-Sso (clone #3-1) (FIG. 3E), and Ty21a-Sso (clone #9-26) (FIG. 3F).

FIGS. 4A-4C. Ty21a-ABC expresses enzymatically active GAD in an arabinose-dependent manner. Ty21a (FIG. 4A), *S. sonnei* 53G form II (FIG. 4B), and Ty21a-ABC (FIG.

4C) were grown in TSB supplemented with 1% trehalose (Tre) and/or 0.75% arabinose (Ara) as indicated above at 37° C. with agitation for overnight to saturation. Cells were harvested and assayed for GAD activity as described in materials and methods. A table summarizing results is shown on the right.

FIGS. 5A-5B. Ty21a-YBC expresses enzymatically active GAD and glutaminase (GLNase) in an arabinose inducible manner. Bacterial cells were grown in TSB supplemented with 1% trehalose and indicated amount of arabinose at 37° C. with agitation for overnight to saturation. Cells were harvested and assayed for GLNase (FIG. 5A) and GAD (FIG. 5B) activity as described in materials and methods. A table summarizing results is shown.

Figure 6:
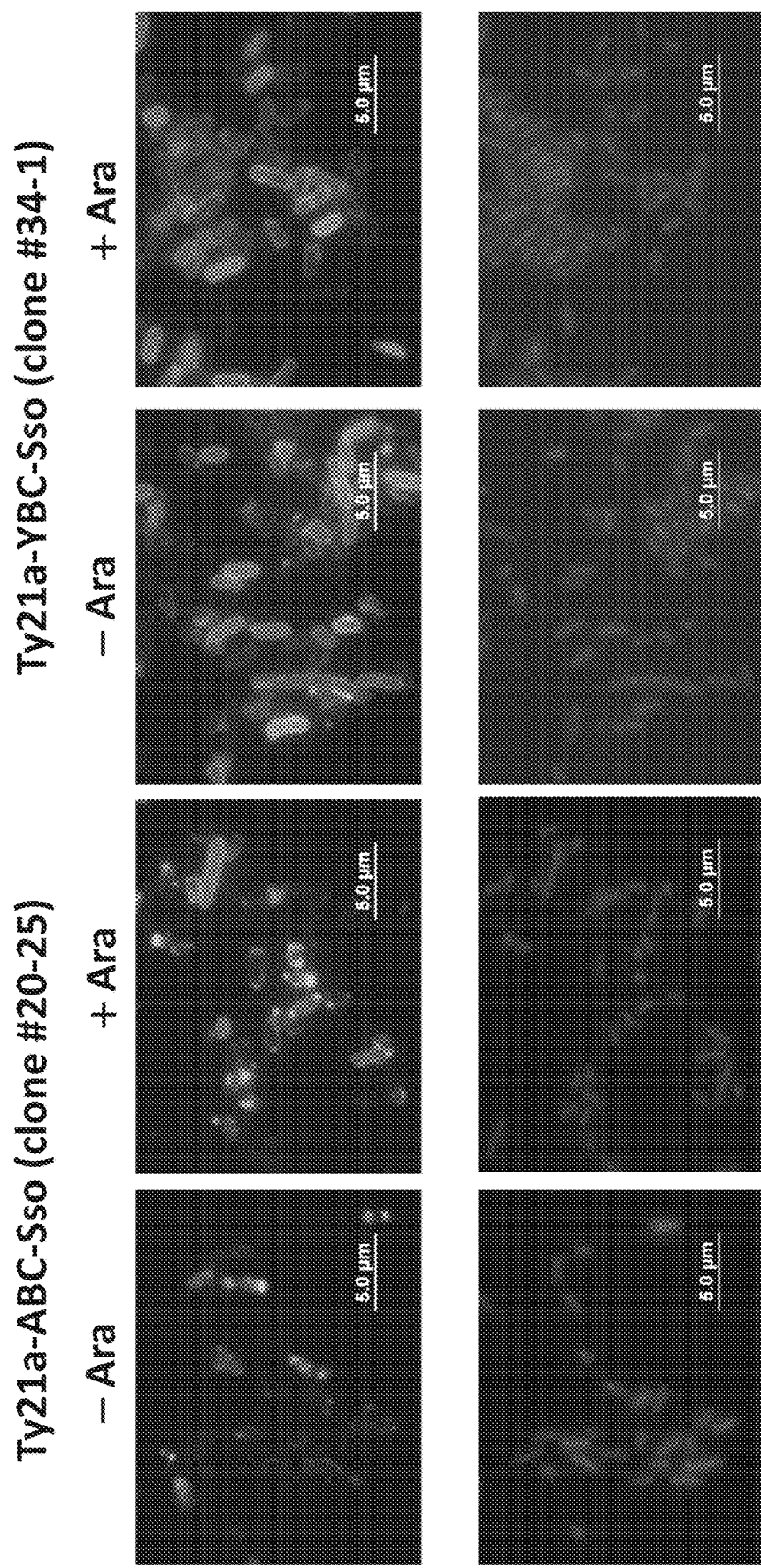

FIG. 6. S. sonnei form I O-antigen expressed from Ty21a-YBC-Sso (clone #34-1) exhibits native form I O-antigen morphology. Ty21a-ABC-Sso (clone #20-25) and Ty21a-YBC-Sso (clone #34-1) were grown in TSB supplemented with 1% trehalose or 1% trehalose and 0.75% arabinose at 37° C. with agitation for overnight to saturation. Cells were fixed by 10% formalin, co-stained with rabbit anti-S. sonnei form I (green), mouse anti-Ty21a (top panel), and DNA inside the cells was counter-stained with DAPI (bottom panel), and visualized by fluorescent microscopy. Images acquired from the same field were superimposed on each other and a representative image is shown for each of the growth conditions for each strain.

Figure 7A:
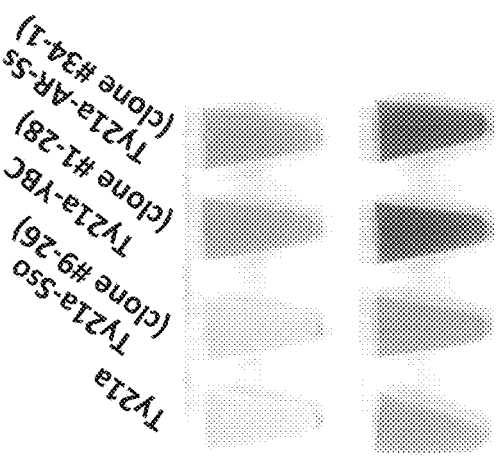
Figure 7B:
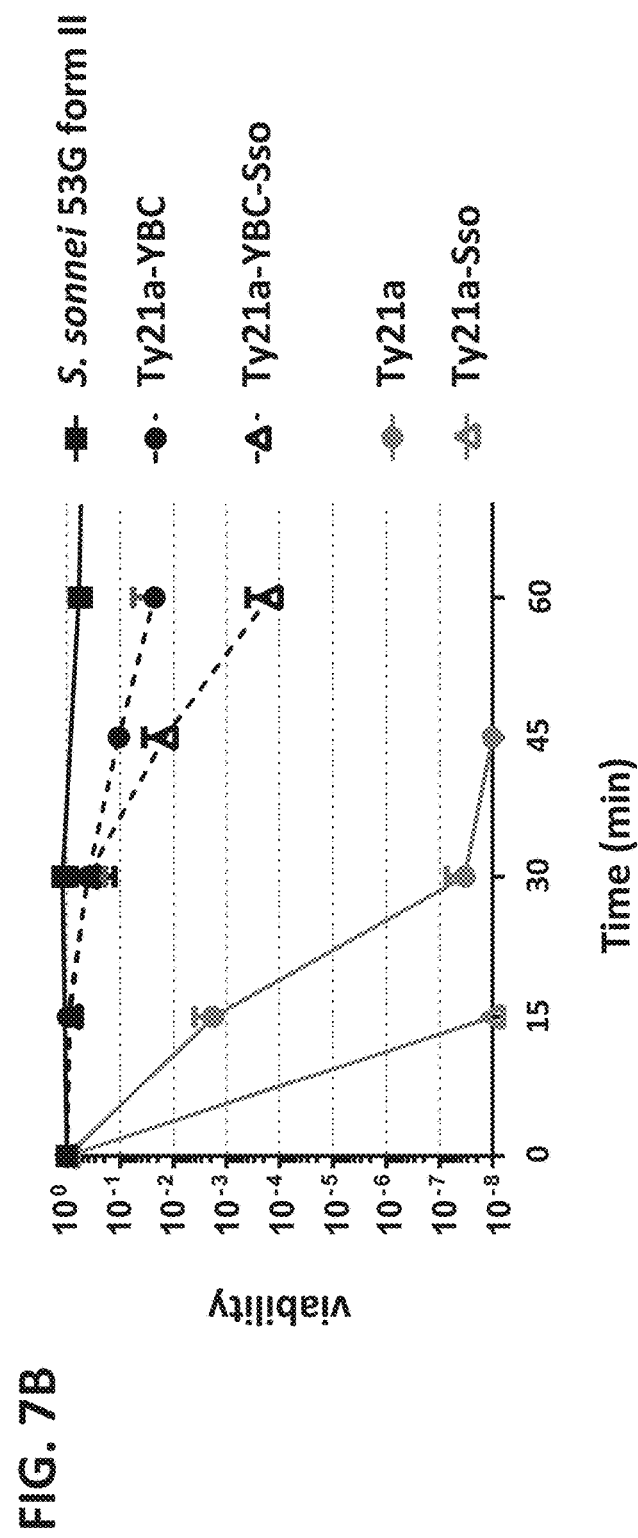

FIGS. 7A-7B. Ty21a-YBC-Sso (clone #34-1) is resistant to acid challenge. Bacterial cells were grown in TSB supplemented with 1% trehalose and 0.75% arabinose at 37° C. with agitation for overnight to saturation. Ty21a and its derivatives from each indicated strains were harvested and assayed for GLNase and GAD activity (FIG. 7A). Cultures were 1:20 diluted into pH 2.5 acid medium containing 1.5 mM glutamine and viable counts were determined for each time point. S. sonnei 53G form II: black squares; Ty21a: gray circles; Ty21a-Sso (clone #9-26): gray open triangles; Ty21a-YBC (clone #1-28): black circles; Ty21a-YBC-Sso (clone #34-1): black open triangles (FIG. 7B). Shown here are results obtained from at least three independent experiments (average±SD).

Figure 8:
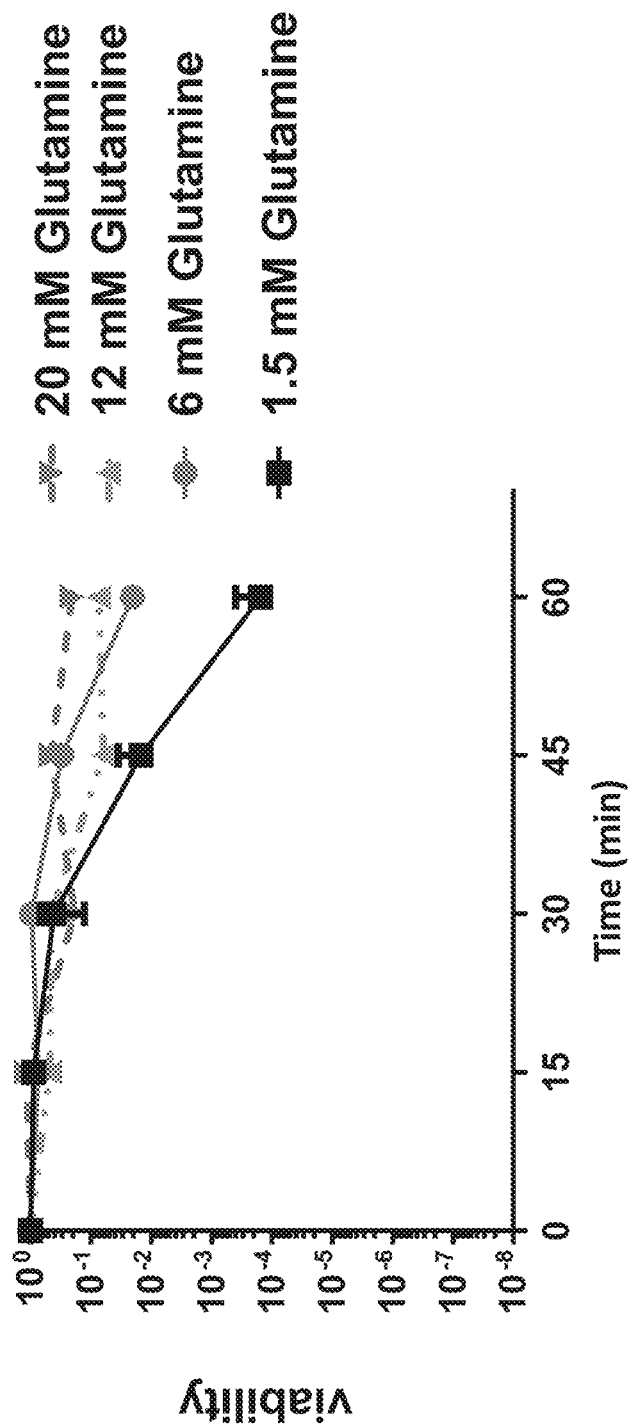

FIG. 8. Increased concentrations of glutamine enhances acid resistance of Ty21a-YBC-Sso (clone #34-1). Ty21a-YBC-Sso (clone #34-1) strain was grown in TSB supplemented with 1% trehalose and 0.75% arabinose at 37° C. with agitation for overnight to saturation. Cultures were 1:20 diluted into pH 2.5 acid medium containing indicated amounts glutamine and viable counts were determined for each time point. Results were obtained from at least duplicate independent experiments (average±SD).

Figure 9B:
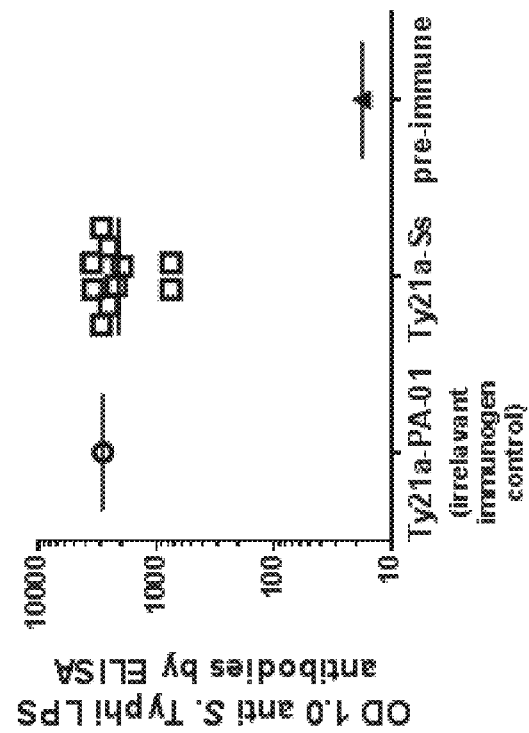
Figure 9A:
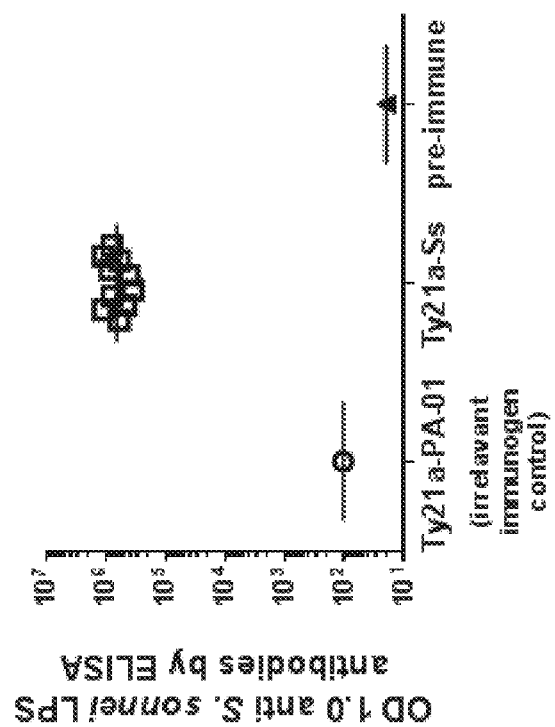

FIGS. 9A-9B. Mice immunized with Ty21a-Sso through the intraperitoneal route produced extremely high levels of serum antibodies against both S. sonnei (FIG. 9A) and S. Typhi (FIG. 9B).

Figures 10A, 10B:
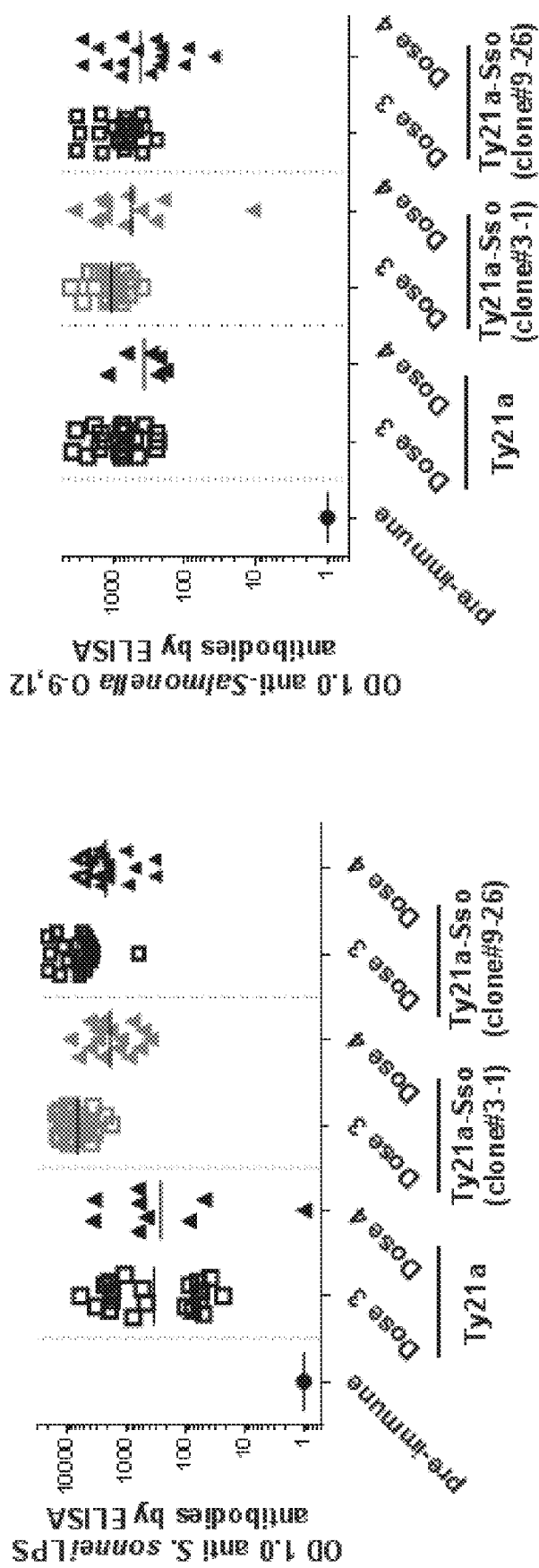

FIGS. 10A-10B. Mice immunized with Ty21a-Sso through the intranasal route produced high levels of serum antibodies against both Shigella sonnei (FIG. 10A) and Salmonella Typhi (FIG. 10B).

Figure 11:
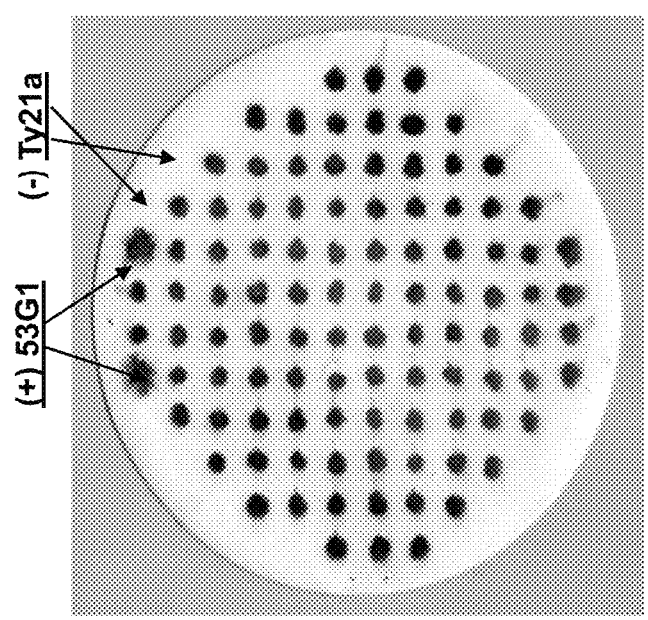

FIG. 11. A representative immunoblot from one of the two random vials from the seed bank for Ty21a-Sso (clone #9-26).

Figure 12:
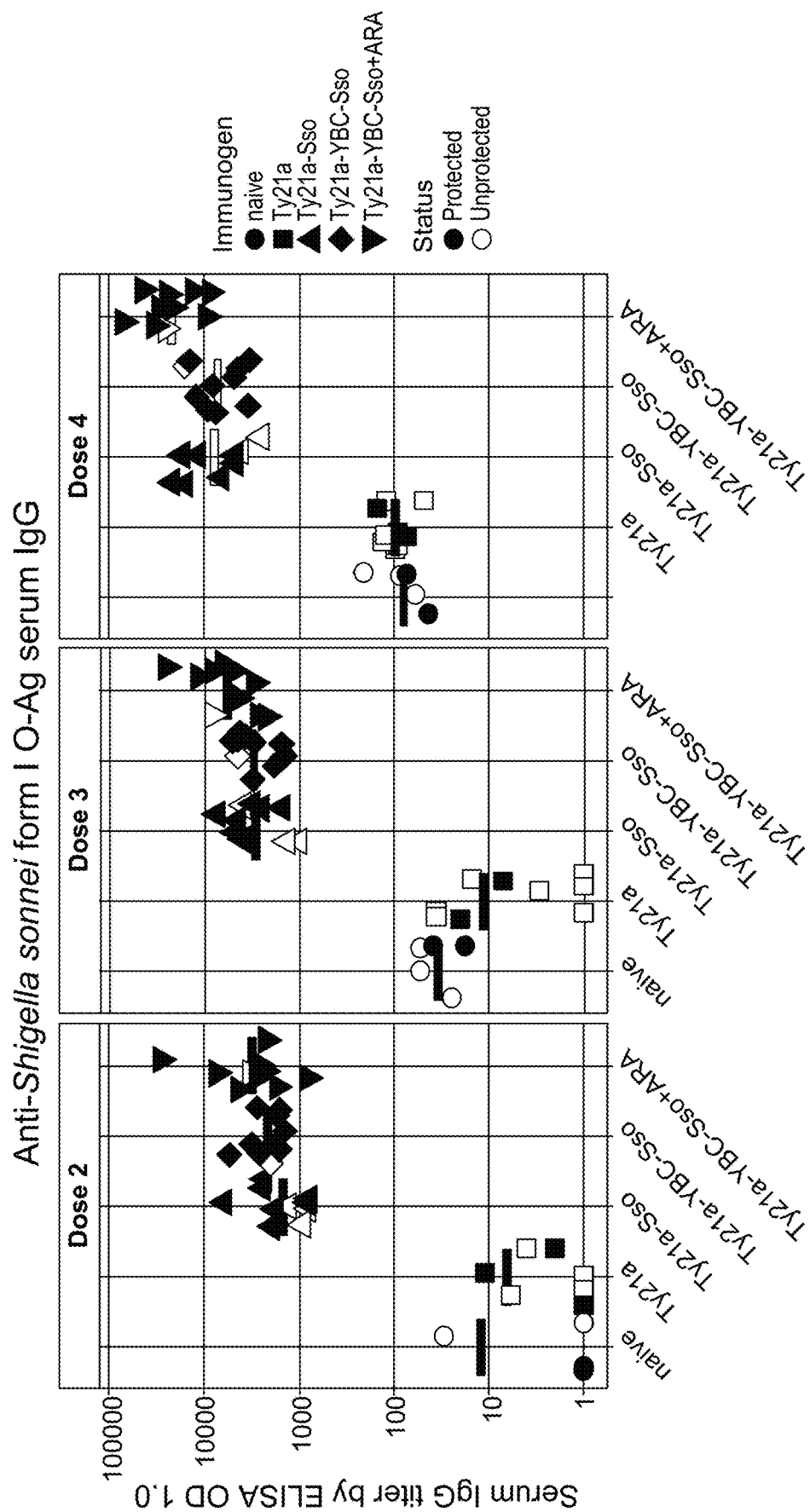

FIG. 12. Serum IgG antibody responses of mice in which Ty21a Sso (clone #9-26) or Ty21a-YBC-Sso (clone #34-1) was administered intranasally was assessed by ELISA.

Figure 13:
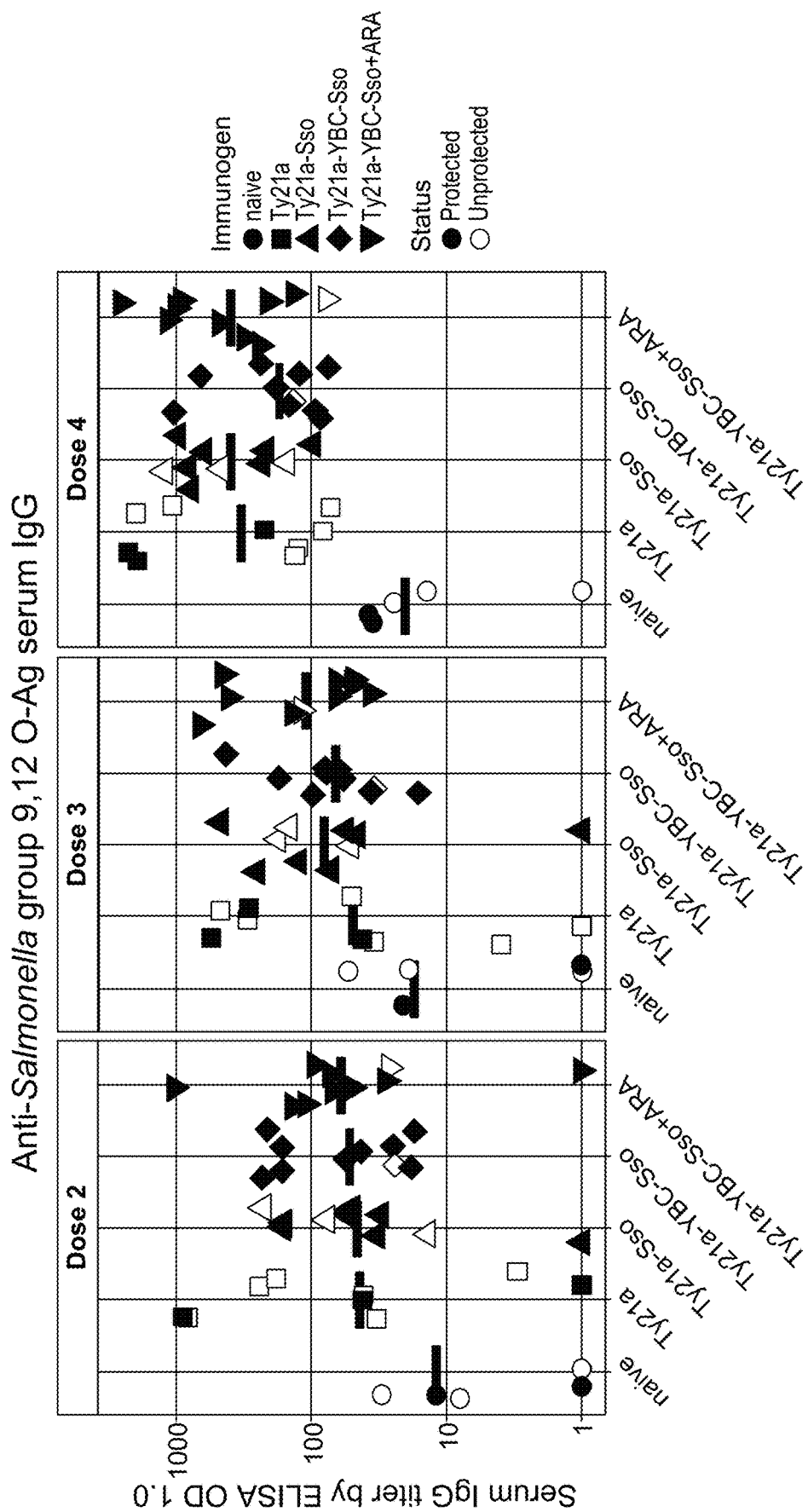

FIG. 13. Serum antibody responses to Salmonella groups O 9, 12-antigens, the native O-antigens expressed on Ty21a surface that induced protective immunity against typhoid fever.

Figure 14:
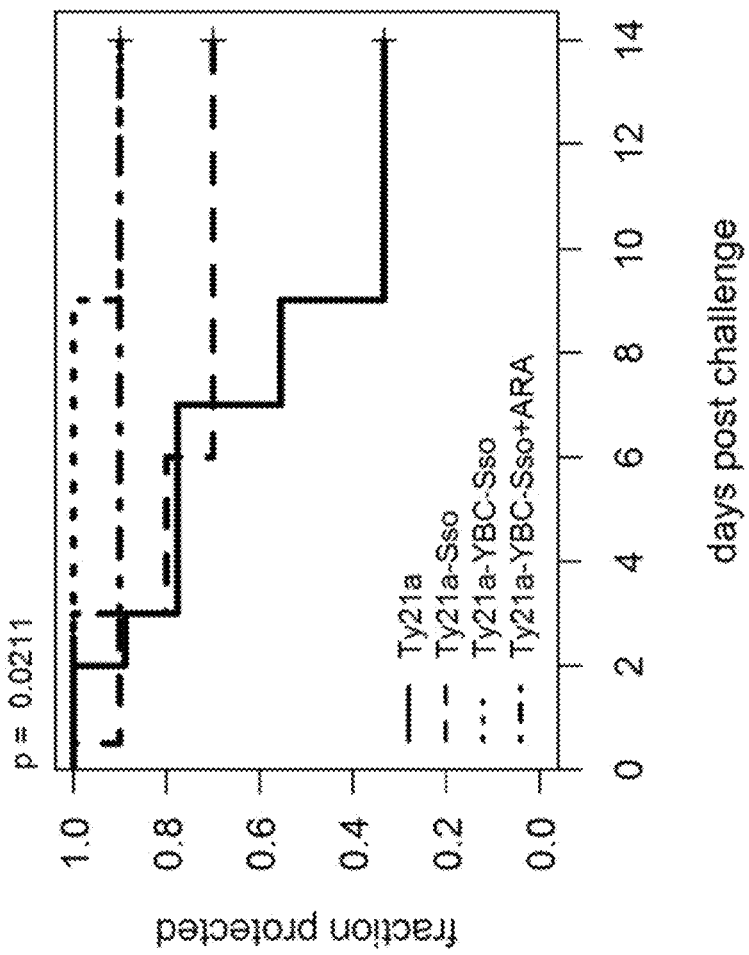

FIG. 14. Shows protection from lethal S. sonnei 53G I infection after administration of Ty21a-Sso or Ty21a-YBC-Sso vaccine.

DETAILED DESCRIPTION

Definitions

"Biosynthetic" as used herein means produced by a process whereby one or more substrates are converted to more complex products within a living organism or cell.

"Deoxyribonucleic acid" or "DNA," is a polynucleotide assembled in a particular sequence that encodes a polypeptide. DNA as used herein can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s).

"Nucleic acid" refers to any one or more nucleic acid segments, e.g., DNA fragments, present in a polynucleotide. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98).

"Sequence identity" as used herein refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a polynucleotide or polypeptide sequence in the comparison window may comprise additions or deletions termed gaps while the reference sequence is kept constant. An optimal alignment is that alignment which, even with gaps, produces the greatest possible number of "identical" positions between the reference and comparator sequences. The terms "sequence identity" and "identical" are used interchangeably herein. Accordingly, sequences sharing a percentage of "sequence identity" are understood to be that same percentage "identical." In some embodiments, the percentage "sequence identity" between two sequences can be determined using the program "BLAST 2 Sequences" which was available from the National Center for Biotechnology Information, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993).

A "gene" refers to a locus (or region) of DNA, which is made up of nucleotides that can that can be transcribed into RNA that encode a polypeptide.

"Gene region" as used herein refers to a location within chromosomal DNA that encodes one or more polypeptides of interest (e.g., an antigen).

"Gene system" as used herein refers to one or more genes that encode one or more polypeptides which when expressed in concert produce a desired effect.

"Variant," as used herein, refers to a polypeptide that differs from the recited polypeptide due to amino acid substitutions, deletions, insertions, and/or modifications.

"Functional variant" includes polypeptides that retain at least some of the properties of the corresponding wild-type polypeptide. For example, in some embodiments, the functional variant of an antigen retains at least 90%, at least 91%, at least 92%, at least 93%, at least 94%, at least 95%, at least 96%, at least 97%, at least 98%, at least 99%, or 100% antigenicity and/or protective immunity of the corresponding wild-type antigen.

"Transgenic" as used herein refers to an organism or cell that comprises a gene, a gene region, and/or a gene system that has been transferred to it by genetic engineering techniques.

"Integrated into" as used herein refers to incorporating a heterologous DNA (e.g., a gene, a gene region, and/or a gene system) into a chromosomal DNA.

"Heterologous" as used herein means from a different organism, cell type or species.

"Transformation," "transfection," and "transduction" refer to methods of transferring nucleic acid (i.e., a recombinant DNA) into a cell. The transferred nucleic acid can be introduced into a cell via an expression vector such as a plasmid, usually comprising components essential for selection, expression of target gene(s), and/or replication in the host cell.

"Stably expressed" as used herein refers to expression of a heterologous gene, a gene region and/or a gene system that has been integrated into chromosomal DNA in a fashion that is reproducible through multiple cell passages and/or under a broad range of physiologic conditions.

"Acid stability" as used herein refers to the ability of cells to remain viable at low pH.

An "antigen" (also referred to as an immunogen) as used herein is a molecule capable of inducing an immune response in a host organism (e.g., a human) that is specific to that molecule.

"Immune response" as used herein means a response in a host organism, e.g., a human, to the introduction of an immunogen (e.g., a transgenic Ty21a of the application) generally characterized by, but not limited to, production of antibodies and/or T cells. In some embodiments, an immune response may be a cellular response such as induction or activation of CD4+ T cells or CD8+ T cells specific for an antigen, a humoral response of increased production of pathogen-specific antibodies, or both cellular and humoral responses.

"Vaccine" as used herein is a composition comprising an immunogenic agent (e.g., an immunogen or antigen) and a pharmaceutically acceptable diluent or carrier, optionally in combination with excipient, adjuvant and/or additive or protectant.

In certain embodiments, when a vaccine is administered to a subject, the immunogen (e.g., a transgenic Ty21a of the application) stimulates an immune response that will, upon subsequent exposure to an infectious agent, protect the subject from illness or mitigate the pathology, symptoms or clinical manifestations caused by that agent. In some embodiments, a therapeutic (treatment) vaccine is given after infection and is intended to reduce or arrest disease progression. In some embodiments, preventive (prophylactic) vaccine is intended to prevent initial infection or reduce the rate or burden of the infection.

"Carrier" as used herein refers to a substance that renders a composition suitable for pharmaceutical use. In some embodiments, the carrier is selected from the group consisting of water, PBS, saline, or any combination thereof. In another embodiment the carrier is selected from the group consisting of sucrose, ascorbic acid, amino acid mixture, lactose, magnesium stearate, or any combination thereof, "Conferring protective immunity" refers to providing to a subject (i.e., an individual) or a human population (e.g., at least 10 subjects) the ability to generate an immune response to protect against a disease (e.g., shigellosis or typhoid fever) caused by subsequent exposure to a pathogen (e.g., a bacteria) such that the clinical manifestations, pathology, or symptoms of disease are reduced during subsequent exposure to the pathogen as compared to a non-treated subject, or such that the rate at which infection, or clinical manifestations, pathology, or symptoms of disease appear within a population are reduced, as compared to a non-treated population.

"Human population" as used herein refers to a group of humans which can be represented by a defined number of subjects, e.g., at least 10 subjects.

"Dose" as used herein refers to a distinct administration event to a subject.

"Immunized" as used herein means sufficiently vaccinated to achieve a protective immune response.

In certain embodiments, as used herein, the term "about" means plus or minus 5% of the numerical value of the number with which it is being used. Therefore, about 85% means in the range of 80% to 90% as described herein.

Compositions

This invention discloses the preparation and use of Ty21a vectors to express foreign immunogens, e.g., *Shigella sonnei* or *E. coli* genes. In some embodiments, the attenuated *Salmonella enterica* serovar typhi vaccine Ty21a as an expression vector for *Shigella sonnei* genes, e.g., stably integrated into the Ty21a chromosome. In some embodiments, the attenuated *Salmonella enterica* serovar typhi vaccine Ty21a as an expression vector for Enterotoxogenic *E. coli* (ETEC) antigens, e.g., stably integrated into the Ty21a chromosome.

In addition to providing bivalent protection against both typhoid fever and shigellosis, integration of an acid resistance cassette provides acid stability and enhances viability of recombinant Ty21a as it passes through the stomach where conditions are acidic, thereby providing for more stable gene expression. This can also eliminate the need for gelatin capsules or liquid formulations and provides temperature stabilization and extended shelf life.

In some embodiments, of Ty21a vector used to express foreign immunogens is a transgenic *Salmonella typhi* Ty21a comprising a heterologous *Shigella sonnei* O-antigen biosynthetic gene region and a heterologous acid resistance biosynthetic gene system, said biosynthetic O-antigen gene region and said acid resistance biosynthetic gene system both being integrated into the *Salmonella typhi* Ty21a chromosome.

In an embodiment, the heterologous *Shigella sonnei* O-antigen biosynthetic gene region of the transgenic Ty21a comprises a wzz gene. In some embodiments, the wzz gene comprises a DNA sequence that shares at least 90%, at least 95%, or 100% sequence identity with the DNA sequence of nucleic acids 4,511,904 to 4,513,010 of SEQ ID NO: 4 or a complementary sequence thereof, the DNA sequence of nucleic acids 4,511,904 to 4,513,010 of SEQ ID NO: 4 or a complementary sequence thereof, or a DNA sequence that encodes a functional variant of the polypeptide encoded by the DNA sequence of nucleic acids 4,511,904 to 4,513,010 of SEQ ID NO: 4 or a complementary sequence thereof.

In an embodiment, the heterologous *Shigella sonnei* O-antigen biosynthetic gene region of the transgenic Ty21a comprises a DNA sequence that shares at least 90%, at least 91%, at least 92%, at least 93%, at least 94%, at least 95%, at least 96%, at least 97%, at least 98%, at least 99%, or 100% sequence identity with the DNA sequence of nucleic acids 4,500,076 to 4,513,461 of SEQ ID NO: 4 or a complementary sequence thereof, the DNA sequence of nucleic acids 4,500,076 to 4,513,461 of SEQ ID NO: 4 or a complementary sequence thereof; or a DNA sequence that encodes a functional variant of the polypeptide encoded by the DNA sequence of nucleic acids 4,500,076 to 4,513,461 of SEQ ID NO: 4 or a complementary sequence thereof.

In an embodiment, the transgenic Ty21a heterologous acid resistance biosynthetic gene system comprises a YbaS gene. In some embodiments, the YbaS gene comprises a DNA sequence that shares at least 90%, at least 91%, at least 92%, at least 93%, at least 94%, at least 95%, at least 96%, at least 97%, at least 98%, at least 99%, or 100% sequence identity with the DNA sequence of nucleic acids 4,503,240 to 4,504,172 of SEQ ID NO: 1 or a complementary sequence thereof; the DNA sequence of nucleic acids 4,503,240 to 4,504,172 of SEQ ID NO: 1 or a complementary sequence thereof, or a DNA sequence that encodes a functional variant of the polypeptide encoded by the DNA sequence of nucleic acids 4,503,240 to 4,504,172 of SEQ ID NO: 1 or a complementary sequence thereof.

In an embodiment, the transgenic Ty21a comprises a nucleic acid insert comprising AraC-YbaS-GadBC-Sso O Ag wzz+. In some embodiments, the AraC-YbaS-GadBC-Sso O Ag wzz+ insert comprises a DNA sequence that shares at least 90%, at least 91%, at least 92%, at least 93%, at least 94%, at least 95%, at least 96%, at least 97%, at least 98%, at least 99%, or 100% sequence identity with the DNA sequence of nucleic acids 4,500,075-4,518,404 of SEQ ID NO:6 or a complementary sequence thereof, the DNA sequence of nucleic acids 4,500,075-4,518,404 of SEQ ID NO:6 or a complementary sequence thereof; or a DNA sequence that encodes a functional variant of the polypeptide encoded by the DNA sequence of nucleic acids 4,500,075-4,518,404 of SEQ ID NO:6 or a complementary sequence thereof.

In some embodiments, the transgenic *Salmonella typhi* Ty21a vector comprises a nucleic acid sequence that shares at least 90%, at least 91%, at least 92%, at least 93%, at least 94%, at least 95%, at least 96%, at least 97%, at least 98%, at least 99%, or 100% sequence identity with the sequence of SEQ ID NO: 1, SEQ ID NO:2, SEQ ID NO:3, SEQ ID NO:4, SEQ ID NO:5, SEQ ID NO:6, or a complementary sequence thereof.

The use of Ty21a as a vector platform to express foreign immunogens derived from other infectious agents as transgenes addresses several significant challenges in the field of vaccine development: 1) The lack of a licensed vaccine for prevention of morbidity and mortality due to shigellosis; 2) The need for a multivalent vaccine that will simultaneously protect against multiple disease agents (e.g., typhoid fever and *S. sonnei* shigellosis), and 3) The need for an easy-to-administer, child-friendly, safe, oral vaccine vector platform for stable expression and administration of multiple foreign antigens, that generates long term efficacy following a rapid immunization regimen and can be distributed without the need for refrigeration. These challenges are addressed by the bivalent typhoid/shigellosis vaccine disclosed herein.

In an embodiment, the transgenic *Salmonella typhi* Ty21a of the invention comprises a heterologous Enterotoxogenic *E. coli* (ETEC) antigen biosynthetic gene region and, optionally, a heterologous acid resistance biosynthetic gene system, said ETEC biosynthetic gene region and said optional acid resistance biosynthetic gene system both being integrated into the *Salmonella typhi* Ty21a chromosome, wherein:

a. heterologous ETEC antigen is stably expressed;
b. one or more heterologous acid resistance enzymes are stably expressed;
c. said transgenic *Salmonella typhi* Ty21a is more stable at pH 2.5 than *Salmonella typhi* Ty21a without the inserted acid resistance biosynthetic gene system;
d. an immune response is elicited against virulent Enterotoxogenic *E. coli* challenge; and/or
e. an immune response is elicited against virulent *Salmonella typhi* challenge.

Methods of Use

As used herein, a "human population" is a designated group of human individuals, e.g., at least two individuals. For example, a human population comprises those individuals participating in a clinical trial, or individuals that have received a vaccine and are then challenged to assess protection.

In certain embodiments, administration of a vaccine or composition of the invention to a human population reduces the incidence of shigellosis, typhoid fever, or both in that human population subsequently exposed to pathogenic *Shigella sonnei* and/or *S. typhi*.

In certain embodiments, a method of treating, preventing, or reducing the incidence of shigellosis and/or typhoid fever in a human subject is disclosed, e.g., comprising oral administration of one or more doses of a vaccine or composition of the invention.

In some embodiments, the administration route is oral or nasal. In some embodiments, the administration (e.g., immunization) and/or infection route is oral (per os). In another embodiment, the administration (e.g., immunization) route is nasal. The major barrier for a live oral vaccine is the extreme low pH the vaccine encounters in the stomach. *Salmonella* does not survive well under conditions <pH 3, while most *E. coli* strains and *Shigella* spp. can maintain viability in stomach for several hours [21,22]. The ability of *Shigella*, and the inability of *Salmonella*, to survive at low pH may partially explain why only 10-100 *Shigella* cells are sufficient to cause infection, while the infective dose for *Salmonella* spp. ranges at ~$10^5$ CFU. *Salmonella* expresses acid tolerance response (ATR) genes in response to moderately low pH, which protect the cells from acid challenge as low as pH 3 [21, 23-26]. Ty21a inherited an rpoS mutation from its parental strain Ty2 [27], and carries other less well defined mutations from the random mutagenesis process during strain attenuation [28]. Perhaps because of these mutations, Ty21a develops a poor ATR response and is particularly sensitive to low pH [29]. However, Ty21a viability is important for vaccine efficacy, as a previous report demonstrated that, when administered orally, live Ty21a elicited stronger and longer lasting immune responses in humans than killed Ty21a [30]. To facilitate the journey from mouth to ileum without being eliminated in the gastric acid environment, Ty21a is presently placed in enteric-coated capsules that withstand gastric low pH. Additionally, when administered as a liquid with a buffer, Ty21a was more protective [12]. On the other hand, capsules are child-unfriendly and adversely impact compliance. Also, the Ty21a liquid formulation has been commercially unsuccessful, in part because it is cumbersome.

To obviate the need for special capsules or liquid formulation in buffer, increase bioavailability, reduce dosage requirements, and increase immunogenicity, Ty21a has been rendered acid stable. There are 5 bacterial acid resistance (AR) pathways, which utilize excess protons to decarboxylate a specific amino acid (e.g. aspartic acid, phenylalanine, lysine, or glutamic acid), and an antiporter that transports the decarboxylated product extracellularly [31,32]. The ability of E. coli, Shigella, Listeria monocytogenes and Lactococcus lactis to withstand extreme acidic pH (below pH 2.5) primarily relies on the most potent AR system, AR2, also known as the glutamate-dependent acid resistance (GDAR) pathway [21,33]. AR2 consists of the enzyme glutamate decarboxylase (GAD), encoded by the homologous genes gadA and gadB, and a membrane bound antiporter, encoded by the gene gadC. The two GAD isoforms, GadA and GadB, consume an intracellular proton to decarboxylate glutamate, producing γ-amino butyric acid (GABA) and $CO_2$ [23, 34-37] while GadC pumps the substrate (glutamate) and product (GABA) in and out of the cell (FIG. 1A and reviewed in [35]). Genes of the two GAD isoforms are located in two distinct chromosomal loci, with gadB and gadC transcribed as a dicistronic operon, and gadA from a separate gene locus [35,38,39]. GadA and GadB are highly similar, with sequence identity of 96.5% at nucleotide level and 98.7% at protein level. Deletion of either gadA or gadB does not affect the cell's AR ability, suggesting these two isozymes are functionally redundant. Recently, a newly discovered glutamine-dependent AR system in E. coli [40] and Lactobacillus reuteri [43] was reported. In E. coli, a previously uncharacterized bacterial glutaminase A, encoded by the gene ybaS, converts glutamine into glutamate in acidic conditions and releases an ammonium, neutralizing an intracellular proton [40]. Interestingly, the antiporter responsible for substrate-product transportation across cell membrane is also GadC [40], consistent with the broad substrate specificity of GadC in vitro [41]. Because the product of glutaminase is precisely the substrate of GAD, the YbaS-GadC and GAD-GadC systems work in concert to convert a glutamine molecule into GABA, neutralizing two protons in the cell (FIG. 1B and [40]), thereby doubling the proton-reducing capacity of the system. This concerted AR system functions more efficiently than the GAD-GadC system alone.

In addition to providing bivalent protection against both typhoid fever and shigellosis, in some embodiments, integration of an acid resistance cassette eliminates the need for gelatin capsules or liquid formulations and provides temperature stabilization and extended shelf life.

Materials and Methods

Bacterial strains and growth conditions. Bacterial strains used or generated in the Examples are listed in Table I. Ty21a was commercially purchased as enteric-coated capsules from Vivotif Berna Vaccine pharmaceutical (Crucell, FL, USA). A seed bank was made in the CY medium (1.2% yeast extract, 2% Hy-Case, 1.2% pepticase, 0.125% $NaH_2PO_4$, 0.33% NaCl, pH 7.2, with 0.2% glucose and 0.005% galactose), which is also adopted by Vivotif for production [10]. Shigella sonnei 53G was a gift from Dr. Dennis J. Kopecko [42]. Form I S. sonnei 53G was selected from form II S. sonnei based on a smooth colony morphology on a tryptic soy agar (TSA) plate at least once before use. Competent E. coli NEB5a cells for cloning were purchased from New England Biolabs (NEB, Ipswich, MA). Ty21a and derivatives were grown in TSA or tryptic soy broth (TSB) supplemented with 0.02% galactose. S. sonnei strains were grown in TSA or TSB. E. coli strains were grown in Luria-Bertaini (LB) broth or agar.

Plasmids. Plasmids used or generated in the Examples are listed in Table I. Standard molecular biology techniques are used for cloning. Enzymes for cloning and Phusion high-fidelity PCR master mix were purchased from NEB. The integrity of all plasmid generated in this study was confirmed by DNA sequencing analysis.

(i) Construction of pMDTV::Sso O Ag (wzz-). Sequences of the S. sonnei form I O antigen gene cluster were PCR amplified from genomic DNA of form I S. sonnei 53G. Primers SalI-wzz-496F (5'-tacagtcGAC ATAGATTTCC AGAGAAAATC AG-3') and BamHI-wzy-D99R (5'-attggatcCA TTGCTCAGTC CGGTTGGT-3') were used to amplify part of wzz gene through wzy. Primers BamHI-wbgV-U14F (5'-attggatccA AGCGCAGCTA TTTAGGATG-3') and XhoI-aqpZ-D5R (5'-acatctcgaG CTGGTTAATT TACGGGGTG-3') were used to amplify full-length wbgV through aqpZ. The two PCR products were first cloned into pUC19-based vector for DNA amplification and sequence verification and then subcloned sequentially into pMDTV vector within SalI-XhoI sites as illustrated in the schematic diagram in (as pWR101 wzz- of FIGS. 2A, 2B).

(ii) Construction of pMDTV::Sso O Ag wzz+. Cloning procedures were the same as that of pMDTV::Sso O Ag (wzz-) except primer SalI-wzz-ml-U100F (5'-TACAgtcgac GCGCTTTGGG AGCTGAAACT-3') was used instead of SalI-wzz-496F so that the PCR fragment included the full-length wzz gene as well a 100-bp upstream sequence containing a putative promoter and ribosome binding site (as pSs046 wzz+ of FIGS. 2A, 2B).

(iii) Construction of pUC19::TviD-AraC-GAD-KanR-VexA. Sequences of tviD, a flippase-recognition target (FRT) site-flanked kanamycin resistant cassette (KanR), and vexA were from pMIDTV [19]. Sequence of AraC and the arabinose-inducible promoter ($P_{ara}$) was from pKD46. Sequences of GadA, GadB and GadC (GAD) were PCR amplified from pGAD containing Shigella flexneri 2a gadA, gadB and gadC gene sequences as a consecutive polycistronic operon. DNA sequences were either subcloned or PCR-cloned into a pUC19 based vector in the order (5' to 3') as described in the plasmid name and the expression of GadA, GadB, and GadC is driven by $P_{ara}$.

(iv) pUC19::TviD-AraC-YbaS-GadBC-KanR-VexA. Sequence of ybaS gene was PCR amplified from S. sonnei 53G genomic DNA and cloned into pUC19::TviD-AraC-GAD-KanR-VexA to replace GadA. Expression of YbaS, GadB, and GadC is driven under $P_{ara}$.

(v) Construction of pTIKV::AraC-YbaS-GadBC-Sso OAg. The NheI-SacII fragment of pMDTV::Lpp-F1V-HlyAs, containing the pGB2 backbone, was used to replace the pUC19 backbone of pUC19::TviD-AraC-YbaS-GadBC-KanR-VexA, resulting pTIKV::AraC-YbaS-GadBC. The XhoI-SpeI fragment of pTIKV::AraC-YbaS-GadBC, containing the KanR-VexA sequence, was subcloned into the XhoI-SpeI fragment of pMDTV::Sso O Ag wzz+ to replace the VexA sequence. The NheI-XhoI fragment of pTIKV::AraC-YbaS-GadBC, containing the TviD, AraC, YbaS, and GadBC sequences, were then subcloned into the NheI-SalI sites of the cloning intermediate, resulting a final product pTIKV::AraC-YbaS-GadBC-Sso O Ag wzz+.

Construction of Ty21a derivatives. Strains generated in the Examples are listed in Table I. Unless otherwise specified, PCR fragment was amplified from the constructed plasmid described above by the Phusion high-fidelity PCR using Primers TviD-2004F (5'-TGATTGCTAA CGTCATGAGC-3') and VexA-1066R (5'-AGAAAGAATT AGTGCCGCGG-3') and genome integration was as described by the k Red recombination-based recombineering technology) [19,43]. The KanR selectable marker was deleted from the chromosomal integrants by transforming cells with pCP20 and selecting for Kans transformants as described [19,44]. Chromosomal integration and selection marker eviction were confirmed by genomic PCR analysis and antibiotics sensitivity tests.

(i) Ty21a-Sso and Ty21a-Sso wzz+. SpeI-linearized plasmids pMDTV::Sso O Ag (wzz-) and pMDTV::Sso O Ag wzz+ were used as PCR templates, resulting in a PCR product that contains the 3' ~500 bp of tviD gene, KanR, the Sso form I O Ag gene cluster without or with wzz expression, and ~1000 bp of the vexA gene. The tviD and vexA sequences provide homology for site-specific DNA recombination. The PCR fragment was integrated into the Ty21a chromosome as described above. Expression of *S. sonnei* form I O antigen and *Salmonella Typhi* 09, 12 antigens were confirmed by Western blot analysis of extracted lipopolysaccharide (LPS, described below) or immunofluorescence assay (described below).

(ii) Ty21a-ABC and Ty21a-YBC. The NheI-SacII fragment of pUC19::TviD-AraC-GAD-KanR-VexA or pUC19::TviD-AraC-YbaS-GadBC-KanR-VexA was liberated by restriction enzymes, gel purified, and used to transform Ty21a for chromosome integration as described above, resulting Ty21a-ABC (short for GadA, GadB, and GadC) and Ty21a-YBC (for YbaS GadB, GadC). Expression of YbaS, GadA/GadB, and GadC upon arabinose induction was confirmed by biochemical activity assays (described below in GAD and glutaminase assays) and cell viability upon acid challenge was assessed by acid resistance assay (described below).

(iii) Ty21a-ABC-Sso and Ty21a-YBC-Sso. SpeI-linearized pTIKV::AraC-YbaS-GadBC-Sso OAg was used as template DNA for PCR amplification. Due to the low PCR amplification yield, PCR primers GadC-1F (5'-ATGGCTACAT CAGTACAGAC-3') and VexA-1066R were used, producing a PCR product comprising GadC, Sso O Ag cluster with full-length wzz, KanR, and VexA. The PCR fragment was integrated into the chromosome of Ty21a-ABC or Ty21a-YBC as described above. Expression of *S. sonnei* form I O antigen and *Salmonella Typhi* 09, 12 antigens were confirmed by Western blot analysis of extracted LPS or immunofluorescence assay. Expression of YbaS, GadA/GadB, and GadC upon arabinose induction was confirmed by biochemical activity assays and cell viability upon acid challenge was assessed by acid resistance assay.

Western blot analyses. O antigens were extracted using an LPS Extraction Kit (iNtRON Bio, Gyeonggi-do, South Korea) followed by proteinase K (NEB) treatment in 10 mM Tris-HCl, pH 8.0 at 37° C. for Overnight. Immediately before loading onto gel, purified LPS was digested by proteinase K in 0.5% SDS at 56° C. for 1 hr. Samples were then heated at 95° C. for 5 min and resolved on a 4-20% Tris-glycine SDS-PAGE gel. Resolved samples from the gel were transferred to a PVDF membrane and blotted with either a rabbit anti-*S. sonnei* serum (Abcam) pre-absorbed with Ty21a and form II *S. sonnei* 53G or a rabbit anti-Ty21a serum (Sim BKL et al., 2015, in submission).

Immunofluorescence assay. Cells were fixed by directly adding formalin (37% formaldehyde) to a bacterial culture to a final concentration of 10% and incubated at ambient temperature for 20 minutes on a rotary shaker. The fixed cells were washed three times with PBS before spotted on a glass slide and air-dried overnight. The slide was blocked with 1% bovine serum albumin (BSA) in phosphate-buffered saline (PBS) at ambient temperature for 30 min before reacting with first antibodies of pre-absorbed rabbit anti-*S. sonnei* form I serum and mouse anti-Ty21a serum diluted in 1% BSA in PBS at 37° C. for 30 min [Sim BKL et al., 2015, submitted for publication]. Alexa Fluor 488-conjugated goat anti-rabbit IgG and Alexa Fluor 564-conjugated goat anti-mouse IgG (Life Technologies) were used as secondary antibodies and mounting fluid containing DAPI (Vector Laboratories, Burlingame, CA) were used for DNA counterstaining. Samples were visualized and images captured on an Olympus DP70 digital microscope camera system and images were processed by DP manager.

Glutaminase and GAD activity assays. Glutaminase and GAD assays were modified from a previously published GAD assay [45]. The glutaminase reagent consisted of 0.1% L-glutamine (Sigma), 9% NaCl, and 0.1 mg/mL bromocresol green (Sigma), pH 3.6 and the GAD reagent consisted of 0.1% L-glutamic acid (Sigma), 9% NaCl, and 5 mg/mL bromocresol green (pH 3.4). 1 OD of cells (defined as the equivalent of 1 mL of culture with an absorbance at 600 nm of 1.0, corresponding to ~$10^9$ viable cells) were pelleted and resuspended in 0.5 mL of glutaminase or GAD reagent. Tubes were incubated at 37° C. for 1 hr. A change of color from yellow to greenish-blue or blue was considered a positive and a yellow color was scored as negative.

Acid resistance assay. Acid buffer (50 mM citric acid, 50 mM phosphoric acid, 0.9% NaCl, pH 2.5) was prepared and sterilized by filtering through 0.2 m. Glutamine was freshly prepared on the day of experiment by dissolving glutamine powder in 1 N HCl to a final concentration of 0.3 M. NaOH was added according to the amount of glutamine added to neutralize the acidity from HCl. Unless otherwise indicated, cells were grown in TSB+0.02% galactose+1% trehalose (Tre)+0.75% arabinose (Ara) at 37° C. for overnight with agitation at 220 rpm. The next day, the saturating culture was diluted 1:20 into acid medium (acid buffer supplemented with 0.75% arabinose and glutamine at indicated concentration) and incubated at 37° C. with agitation. At indicated time points, an aliquot of culture was taken out, diluted in DPBS (Hyclone), and cultures with proper dilution were either spotted 5 μL/spot (for a spot assay) or spread 100 μL/plate (for a plate enumeration) on TSA plate. Plates were incubated at 37° C. for 1 day and bacterial growth was quantified. Cell viability at a given time point is expressed as the fraction of mean viable counts with respect to that at 0 time point.

Results

Construction of a recombinant Ty21a strain with a stable chromosomal integrant of S. sonnei form I O-antigen gene cluster has be disclosed by inventors including a co-inventor herein [19]. It was found however, that Ty21a strain was constructed from a lab strain that had been propagated over decades and the donor DNA for S. sonnei form I O-antigen genes was a plasmid derived from multiple subclonings [46] and has an IS element interruption at the wzz gene compared with the sequences from another independently published report, pSs046 [47]. Therefore, we re-constructed the vaccine strain from a cell bank made from commercially purchased Ty21a Vivotif® pharmaceutical capsules (Crucell) and *S. sonnei* 53G form I [42] to ensure that the vaccine strains disclosed herein have trackable pedigrees.

The transgenic constructs disclosed herein have at least the following improvements as compared to the Ty21a-Sso combinatorial vaccine candidate in Int. Publ. number WO2014043637 A1): (1) inclusion of the full-length *S. sonnei* wzz gene that encodes the O-antigen length control protein together with the rest of the gene cluster, which renders *S. sonnei* form I O-antigen expressed on Ty21a surface exhibiting better morphologically resemblance to the native form on *S. sonnei*; (2) co-expression from Ty21a chromosome with the *S. sonnei* form I gene cluster a concerted glutamine/glutamate-dependent acid resistance genes, including acid-activated glutaminase YbaS, glutamate decarboxylase GadB, and glutamate-GABA antiporter GadC, which enhance acid resistance of the said vaccine strain and presumably facilitate gastric transit of the bacterial vaccine and induce more potent and long-lasting immune responses in vaccines.

Immunogenicity of Recombinant Ty21a-Ss vaccine strains in mice was assessed. Example 9 provides the results from ELISA assays of the sera of mice in which Ty21a-Sso (clone #9-26) and Ty21a-YBC-Sso (clone #34-1) was administered intranasally. Example 10 provides the results of serum antibody response of immunized mice to *Salmonella* groups O 9, 12-antigens, the native O-antigens expressed on Ty21a surface that induced protective immunity against typhoid fever. Examples 9 and 10, taken together, demonstrate that the *S. sonnei* form I O-antigen expressed on the cell surface of the recombinant vaccine strains was immunogenic when administered through mucosal routes. Meanwhile, recombinant Ty21a-Sso strains retained the immunogenicity of Ty21a and stimulated anti-*Salmonella* groups 9, 12 O-antigens at a level similar to the Ty21a vector. Moreover, co-expression of the AR genes did not affect the immunogenicity of the *S. sonnei* form I or the *Salmonella* groups 9, 12 O-antigens. Activation of AR genes slightly enhanced the antibody titers to both *S. sonnei* form I and *Salmonella* groups 9, 12 O-antigens, although the differences are not statistically significant.

EXAMPLES

Example 1

Stable Integration and Expression of *S. sonnei* (Sso) Form I O-Antigen from Ty21a Chromosome, Free of Antibiotic Resistance Gene The sequence of form I O-antigen gene cluster from the genomic DNA of *S. sonnei* 53G form I was amplified and inserted it into the silent Vi gene region of Ty21a chromosome between the tviD and vexA sequences using genetic recombineering technology [19] (FIGS. 2A-2C). The insert spanned from the wzz ORF through the end of the aqp gene, with the exception of the insertional element IS630 between the wzy and wbgVgenes. Because of the divergence of wzz in two published reports [46,47], both an wzz− strain resembling the previous Ty21a-Ss construct [19], in which the gene cluster encompasses from the 3'-612 bp of wzz through the end of aqp genes, and a wzz+ strain, in which full-length wzz sequence and a 100-bp upstream sequence were included in the insert, were constructed. The 100-bp upstream sequence covers the conserved 5' border of O-antigen clusters [47] and a Shine-Dalgarno consensus sequence immediately upstream to wzz drives wzz expression.

After chromosome integration was confirmed, the selectable antibiotics marker was deleted from the insert, leading to final, marker-less chromosomal integrants, designated as Ty21a-Sso (clone #3-1) and Ty21a-Sso wzz+(clone #9-26). There were 6 nucleotide polymorphisms identified within this cloned *S. sonnei* form I gene cluster sequence in comparison to the previous published sequence (pWR101) [46]. Five of the polymorphisms were non-synonymous mutations and one was located within intergenic region. By DNA sequencing of independently amplified PCR fragments it was confirmed that these polymorphisms were present in *S. sonnei* 53G form I genome. Moreover, three of the polymorphisms are present in the sequence of pSs046 [47]. Therefore, these polymorphisms arose from variation between lab isolates.

Example 2

*S. sonnei* Wzz Gene Promote Uniform Distribution of *S. sonnei* Form I O-Antigen on Ty21a Cell Surface, Resembling the Native *S. sonnei* Form I O-Antigen Expression of the *S. sonnei* form I O-antigen in the wzz− Ty21a-Sso (clone #3-1) and wzz+Ty21a-Sso (clone #9-26) strains was examined. By Western blot analyses, both clones expressed *S. sonnei* form I O-antigen (FIG. 3A) at comparable levels. Similar to [19], the majority of the form I O-antigen was expressed in the form of group 4 capsule, although a low level of LPS form was detected. Despite the expression of *S. sonnei* form I O-antigen on the cell surface, the expression of *Salmonella* groups O 9, 12-antigen from the two Ty21a-Sso strains were shown to be of similar levels as compared to that of Ty21a (FIG. 3B). O-antigen expression was further visualized by immunofluorescence assay (IFA). The results showed that with Ty21a (FIG. 3C, *Salmonella* groups 9 and 12 O-antigens only) and *S. sonnei* (FIG. 3D, form I O-antigen only) the antibodies were specific and the native O-antigens are expressed uniformly on the cell surface. Both Ty21a-Sso (clone #3-1) and Ty21a-Sso (clone #9-26) expressed both *Salmonella* groups O 9, 12-antigen and *S. sonnei* form I O-antigen on the cell (FIGS. 3E, 3F). Of note, both Ty21a-Sso (clone #3-1) and Ty21a-Sso (clone #9-26) expressed *S. sonnei* form I O-antigen at 100% of cells examined. However, the morphology of the expressed *S. sonnei* form I O-antigen was slightly different. In the wzz− Ty21a-Sso (clone #3-1) strain, *S. sonnei* form I O-antigen often appeared as non-homogeneous, punctuated dots on cell surface (FIG. 3E). On the other hand, *S. sonnei* form I O-antigen showed a much more uniformed expression in the wzz+Ty21a-Sso (clone #9-26) (FIG. 3F). Similarly, uniformed expression was also observed from another independently generated wzz+Ty21a-Sso clone (data not shown). These results show that *S. sonnei* wzz contributes to the even distribution of *S. sonnei* O-antigen along cell surface. Co-expression of wzz in Ty21a might also help the cell present *S. sonnei* form I O-antigen in a manner more similar to the native form I O-antigen.

Example 3

Stable Integration and Expression of Acid Resistance Genes in Ty21a to Enhance Cell Viability AR genes were expressed in Ty21a vaccine candidates to enhance cell viability at low pH in the stomach, thereby augmenting its immunogenicity and protective efficacy. Expression of the AR2 genes gadA, gadB, and gadC in *E. coli* and *Shigella* is under a series of complex regulation and that of ybaS has yet to be characterized. Activation of the AR2 pathway is dependent on the alternative sigma factor, rpoS, which is mutated and only partially functional in Ty21a.

The arabinose-controlled promoter, $P_{ara}$, which responds quickly to the inducer and the activated arabinose-bound transcription factor AraC activates robust gene transcription, was used in the constructs generated in this Example.

The AraC-$P_{ara}$-*S. flexneri* GadABC cassette was integrated into the vi locus of Ty21a chromosome, replacing the tviE ORF, using the recombineering technology. The final, marker-less, clone was designated Ty21a-ABC (clone #2-2) and the integrated sequence was confirmed by genomic PCR. To confirm that the integrated genes were expressed and enzymatically active, Ty21a-ABC (clone #2-2) was subjected to a modified GAD assay, in which the Triton X-100 was omitted from the original GAD reagent one [45]. In the absence of Triton X-100, the cell remains intact and only a functional GadC can transport glutamate into the cell. Therefore, the modified GAD assay tests simultaneously both the ability of GadA and/or GadB to decarboxylate glutamate and the ability of GadC to transport the substrate.

Bromocresol green in the GAD reagent served as a pH indicator. Cells from culture were resuspended in the modified GAD reagent and reactions that turned greenish-blue in color were scored as GAD+. Ty21a, Ty21a-ABC (clone #2-2), and *S. sonnei* 53G form II were grown in TSB or TSB supplemented with 1% trehalose (Tre) and/or 0.75% arabinose (Ara) at 37° C. with aeration overnight. *Salmonella* and *Shigella* produced alkalinic byproducts in TSB; and the overnight culture was around pH 8. Tre and Ara supported acid fermentation of *Shigella*; and Tre supported acid fermentation of *Salmonella* without inhibiting $P_{ara}$ activity through catabolite repression. The resulting saturating culture was moderately acidic, at around pH 5.5. Ty21a did not encode a GAD enzyme and was GAD—in all culture conditions (FIG. 4, upper panel). Native gadA, gadB, and gadC genes in *Shigella* were quickly induced by acid. The GAD activity in *S. sonnei* 53G was positive for all culture conditions but cells from TSB alone showed lower activity (FIG. 4, middle panel). GAD activity of Ty21a-ABC (clone #2-2) was greatly induced by Ara, and the presence of Tre did not inhibit it (FIG. 4, bottom panel). Ty21a-ABC (clone #2-2) grown in TSB or TSB+Tre turned slightly GAD+, indicating low levels of leaky expression. The integrated transgenes were expressed and enzymatically active in Ty21a-ABC (clone #2-2) in a controlled manner.

Example 4

Stable Integration and Expression of Glutaminase Gene ybaS in Ty21a to Further Enhance Cell Viability Database search revealed that *Shigella* genome encodes a highly conserved ybaS gene, with only 2 out of 310 amino acids of the *S. sonnei* YbaS different from the *E. coli* YbaS enzyme. To construct a concerted glutaminase-GAD AR system, the CDS of ybaS was cloned from *S. sonnei* genomic DNA to replace that of gadA in the AraC-$P_{ara}$-GadABC cassette and integrated the resulting AraC-$P_{ara}$-YbaS-GadBC cassette into Ty21a chromosome using recombineering technology. The resulting final, marker-less, strain was designated as Ty21a-YBC (clone #1-28). Gene integration at the DNA level was confirmed by genomic PCR and enzymatic activities of the transgenes were confirmed by the modified GAD (FIG. 5A) and glutaminase (FIG. 5B) assays. Ty21a-YBC (clone #1-28) expressed both GAD and glutaminase activities induced by arabinose, while Ty21a-ABC (clone #2-2) only exhibited arabinose-induced GAD but not glutaminase activity. The negative control Ty21a expressed none, while the positive control *S. sonnei* form II expressed both enzymes and did not need arabinose to induce expression.

Example 5

Construction of an Acid Resistant Ty21a Expressing *S. sonnei* Form I O-Antigen

A Ty21a-Sso strain that is acid resistant was constructed. Because the size of an insert containing both the AR cassette and *S. sonnei* form I O-antigen gene cluster is too large for PCR-amplification, the acid resistant Ty21a-Sso strains were generated by stably integrating the wzz+*S. sonnei* form I O antigen expression cassette into the chromosome of Ty21a-ABC (clone #2-2) and Ty21a-YBC (clone #1-28) using gadC and vexA as homologous sequences for recombination. The resulting final, marker-less, strains were designated as Ty21a-ABC-Sso (clone #20-25) and Ty21a-YBC-Sso (clone #34-1).

Because the arabinose-induced AR genes are upstream to the *S. sonnei* form I O antigen gene cluster, it was determined whether the presence of arabinose affects 0-antigen expression. Strains were grown overnight in the absence or presence of 1% arabinose and 0.75% arabinose and the saturating cultures were visualized at single cell level using IFA (FIG. 6). When arabinose was present in the culture medium, *S. sonnei* form I O antigen expressed on Ty21a-ABC-Sso (clone #20-25) exhibited a punctuated pattern similar to that from the wzz− Ty21a-Sso (clone #3-1). On the other hand, expression of *S. sonnei* form I O antigen in Ty21a-YBC-Sso (clone #34-1) was not affected by arabinose; the cell displayed uniformed form I O antigen on cell surface morphologically similar to that from *S. sonnei* form I and the wzz+Ty21a-Sso (clone #9-26) in the presence and absence of arabinose. Based on this morphological advantage, Ty21a-YBC-Sso (clone #34-1) was further tested as a candidate vaccine strain.

Example 6

Ty21a-YBC-Sso is Acid Resistant

The ability of Ty21a-YBC-Sso (clone #34-1) to survive at pH 2.5 was tested. Although Tre is not required for transgene expression, *Salmonella* needs acid fermentation to induce ATR, a prerequisite for acid resistance. Bacterial strains were grown in TSB+Tre+Ara with agitation to stationary phase and the strains showed the expression pattern of glutaminase and GAD activities shown in FIG. 7A. Cultures were diluted 1:20 in acid medium at pH 2.5 in the presence of 1.5 mM glutamine. Cultures were grown at 37° C. with agitation and viability was examined at the indicated time point (FIG. 7B). *S. sonnei* 53G form II maintained ~100% viability after 1 hr incubation at pH 2.5 (black squares) and ~50% of the cells were still viable after 2 hr (data not shown). In contrast, Ty21a and Ty21a-Sso (clone #9-26) survived poorly at low pH. Cell viability was reduced by ~$10^3$-fold for Ty21a at 15 min and >$10^7$-fold by 30 min (gray circles). Cell viability was further reduced in Ty21a-Sso (clone #9-26), with no viable colony recovered even after 15 min exposure to acid at pH 2.5, equivalent to a >$10^8$-fold reduction in viability (gray open triangles). Synthesis of the form I O-antigen may impose metabolic burden to the cell. Ty21a-YBC (clone #1-28) maintained greater than 50% viability at 30 min and ~10% at 45 min (black squares). However, the viability dropped to ~1% at 1 hr and no viable colony was recovered after 2 hr (data not shown). Ty21a-YBC-Sso (clone #34-1) exhibited similar acid resistance as Ty21a-YBC (clone #1-28) at 30 min, maintaining ~50% viability. However, the cell viability quickly deteriorated, with ~1% and ~$10^{-5}$ of cells viable at 45 min and 1 hr, respectively (black open triangles). Increasing concentrations of glutamine in acid medium improved Ty21a-YBC-Sso (clone #34-1) survival. With 6 mM glutamine in the pH 2.5 medium, cell survival at 1 hr improved to ~0.1%, and, at 12 mM and 20 mM glutamine, nearly 1% and 10% of cells remained viable after 1 hr at pH 2.5 (FIG. 8). The ability of Ty21a-YBC (clone #1-28) and Ty21a-YBC-Sso (clone #34-1) vaccine strains to survive low pH was inferior to *S. sonnei*, however both strains expressed comparable levels GAD and glutaminase activities to that in *S. sonnei*. This result suggests that the AR system alone is necessary but insufficient to support acid resistance of Ty21a. These results showed that expression of the concerted glutaminase-GAD AR system improved acid resistance and cell viability.

Example 7

Immunogenicity of Ty21a-Sso in Mice 10 mice were immunized intraperitoneally with 3 doses of Ty21a-Sso (clone #3-1), 5×$10^7$ CFU/mouse at 2-week intervals. Two weeks after the $3^{rd}$, high levels of serum IgG antibodies against both *S. sonnei* form I O-antigen and *S. Typhi* groups 9, 12 O-antigen by ELISA at OD 1.0, with geometric mean titers at 666,151 (range 360,341-1,111,200) and 2,103 (range 755-3,529), respectively, were detected in the mice. In comparison, a pooled serum obtained from mice immunized with a Ty21a strain containing an irrelevant antigen (Ty21a-PA-01) through the same dose regimen and immunization route produced negligible anti-*S. sonnei* serum IgG antibodies (ELISA OD 1.0 titer was $10^6$) but comparable levels of anti-*S. Typhi* antibodies (ELISA OD 1.0 titer was 2,864) (FIGS. 9A-9B).

To assess if Ty21a-Sso is immunogenic when introduced via the mucosal route, and to compare the wzz– strain Ty21a-Sso (clone #3-1) and the wzz+ strain Ty21a-Sso (clone #9-26), three groups of 20 mice were immunized intranasally with 4 doses of 1×$10^9$ CFU/mouse Ty21a, Ty21a-Sso (clone #3-1), and Ty21a-Sso (clone #9-26) at 2-week interval. 2 weeks after the $3^{rd}$ and the $4^{th}$ doses, sera were collected and serum IgG levels assessed by ELISA at OD 1.0. The Ty21a vector control induced serum IgG antibodies against *S. sonnei* form I O-antigen at a level similar to that of Ty21a-PA-01 (FIG. 10A), with the geometric mean titers of 340 (range 23-5,823) and 523 (range 48-3,393) for the $3^{rd}$ and $4^{th}$ dose, respectively, as compared to 106. Both Ty21a-Sso (clone #3-1) and Ty21a-Sso (clone #9-26) induced serum IgG antibodies at a significantly higher level than the Ty21a control, with geometric mean ELISA OD 1.0 titers at 6,321 (range 1,730-14,776) and 6,429 (range 611-20,451) after the $3^{rd}$ dose, and 1,815 (range 511-8839) and 2,200 (range 317-7,218) after the $4^{th}$ dose, respectively. The antibody levels were higher than that from a previously published LPS-protein conjugated vaccine candidate, which showed protection against *S. sonnei* infection in guinea pigs [20]. The present results showed that Ty21a-Sso induced mucosal immune responses.

Example 8

Recombinant Ty21a-Ss s Vaccine Strain Maintains Stable Expression of *S. sonnei* Form I O-Antigen for Up to 200 Generations A genetic seedbank was generated for the vaccine strain Ty21a-Sso (clone #9-26). Characterization of the Ty21a-Sso seedbank and the specification are as listed in Table II. Two random vials from the seed bank were characterized as previously published [50]. Ty21a (Vivotif), *S. enterica* serovar *Typhi* strain Ty2, and *E. coli* strain HB101 were controls. All microbiological, biochemical, immunological, and genetic properties examined were as expected. The stability of the *S. sonnei* form I O-antigen expression in Ty21a-Sso was also examined (FIG. 11). Cells were grown under non-selective conditions for a total of 200 generations. 100 colonies from each culture were plated onto a TSA plate, transferred to a nitrocellulose membrane, and analyzed for *S. sonnei* form I O-antigen expression by colony immunoblot. All of 100 colonies of Ty21a-Sso (clone #9-26) tested retained *S. sonnei* form I O-antigen expression, demonstrating 100% stability of the chromosomally integrated genes even after 200 generations of growth. Characterization of Ty21a-Sso seed bank showed that all properties of the strain are as expected and the *S. sonnei* form I O-antigen remained stably expressed in 100% of the colonies after 200 generations of growth. The bacterium was grown at high dilution in TSB for ~24 h, which represents ~25 generation of growth. Each culture was serially diluted to ~100 CFU/ml and grown for an additional 24 h, for a total of 150 generations. The resulting cells from that point were plated on TSA, grown overnight at 37° C. (another ~25 generations), and 100 individual colonies were patched onto a new TSA plate for growth overnight at 37° C. The resulting colonies from agar plates, which have gone through a total of 200 generations of growth, were transferred to a nitrocellulose membrane and analyzed by standard immunoblotting procedures using rabbit polyclonal antisera against *S. sonnei* form I.

Example 9

Immunogenicity of Recombinant Ty21a-Sso and Ty21a-YBC-Sso Vaccine Strains in Mice To assess the immunogenicity of Ty21a-Sso (clone #9-26) and Ty21a-YBC-Sso (clone #34-1) administered through a mucosal route, four groups of 10 mice were immunized intranasally with 4 doses of 1×$10^9$ CFU of Ty21a, Ty21a-Sso (clone #9-26), Ty21a-YBC-Sso (clone #34-1, AR gene not expressed under this condition), and Ty21a-YBC-Sso clone (#34-1) grown in the presence of trehalose and arabinose (AR genes activated; thereafter referred to Ty21a-YBC-Sso+ARA) at 2-week intervals. Serum samples were obtained at 2 weeks after doses 2, 3, 4 and serum IgG antibody responses were assessed by ELISA.

For mice immunized with Ty21a, the geometric mean OD 1.0 (serum dilution at which the optical density was 1.0) titers (GMT) of anti-*S. sonnei* form I O-antigen antibodies were 2.5 (range 1-16), 6.9 (range 1-37), and 62.8 (range 1-149) after 2, 3, and 4 doses of immunization, respectively (FIG. 12, squares). These values were not statistically different from that obtained from naïve mice of the same age, with GMTs at 2.0 (range 1-30), 34.6 (range 18-54), 80.3 (range 43-207) (FIG. 12, circles). In contrast, mice immunized with Ty21a-Sso (FIG. 12, triangles), Ty21a-YBC-Sso (FIG. 12, diamonds), and Ty21a-YBC-Sso (FIG. 12, inverted triangles) produced significantly higher serum IgG titers of anti-*S. sonnei* form I O-antigen, and the titers were progressively higher with increasing number of immunizations ($p<0.05$ by Wilcoxon Rank Sum test). All mice received $1\times10^9$ CFU. For example, at 2 weeks after dose 4, the GMTs to *S. sonnei* form I O-antigen of mice immunized with Ty21a-Sso, Ty21a-YBC-Sso, and Ty21a-YBC-Sso+ARA were 7,909.5 (range 2,560-21,700), 7,202.4 (range 3,363-15,910), and 23,020.8 (range 8,521-71,575), respectively. Sera were collected 2 weeks after doses 2, 3, 4 and antibody responses to extracted *S. sonnei* LPS were measured by ELISA OD 1.0. Sera from 5 un-immunized, naïve mice (circles) of the same age were also collected and measured as negative controls. Each point represents an individual mouse and the intensity of the point indicated whether the mouse was protected (dark) or unprotected (light) from the challenge. The GMT for each group is indicated by a horizontal bar.

Example 10

Serum Antibody Responses to *Salmonella* Groups O 9, 12-Antigens

The serum antibody responses to *Salmonella* groups O 9, 12-antigens, the native O-antigens expressed on Ty21a surface that induced protective immunity against typhoid fever were also examined (FIG. 13). Ty21a-Sso and Ty21a-YBC-Sso immunized through mucosal route generated high antibody responses to Ty21a O-antigens. Sera from mice immunized with Ty21a (squares), Ty21a-Sso (triangles), Ty21a-YBC-Sso (diamonds), Ty21a-YBC-Sso+ARA (inverted triangles), or naïve mice of the same age (circles) were collected 2 weeks after doses 2, 3, 4 and antibody responses to extracted Ty21a LPS (*Salmonella* groups 9, 12 O-antigens) were measured by ELISA OD 1.0. Each point represents an individual mouse and the intensity of the point indicated whether the mouse was protected (dark) or unprotected (light) from a lethal *S. sonnei* 53G form I challenge. The GMT for each group is indicated by a horizontal bar.

For mice immunized with Ty21a, the geometric mean titers of anti-*Salmonella* groups 9,12 O-antigens serum IgG were 53.9 (range 1-864), 54.5 (range 1-545), and 328.3 (range 72-2,295) at 2 weeks after doses 2, 3, and 4, respectively (FIG. 13, squares). We observed that Ty21a-Sso (FIG. 13, triangles), Ty21a-YBC-Sso (FIG. 13, diamonds), and Ty21a-YBC-Sso+ARA (FIG. 13, inverted triangles) induced anti-*Salmonella* groups 9, 12 O-antigen serum IgG at comparable levels. At 2 weeks after dose 4, the GMTs were 421.6 (range 98-1,241), 182.3 (range (74-1,030), and 426.8 (range 78-2,539) for Ty21a-Sso, Ty21a-YBC-Sso, and Ty21a-YBC-Sso+ARA. These antibody levels were significantly higher than that from the naïve mice (FIG. 13, circles), with a GMT of 13.6 (range 1-38).

Example 11

Ty21a-Sso and Ty21a-YBC-Sso Protected Mice from Lethal *S. sonnei* 53G I Infection The immunized mice described in Example 9 were challenged six weeks after dose 4 with a lethal infection of *S. sonnei* 53G form I by intranasal instillation ($1.2\times10^9$ CFU—approximately 120 LD50) and monitored daily for 14 days. Only 3 out of 9 mice immunized with Ty21a (FIG. 14, solid line) survived the challenge, while 7/10, 9/10, and 9/10 mice immunized with Ty21a-Sso (FIG. 14, dashed line), Ty21a-YBC-Sso (FIG. 14, dotted line), and Ty21a-YBC-Sso+ARA (FIG. 14, dot-dash line) survived and remained healthy throughout the 14-day monitoring period. The difference was statistically significant ($p=0.0211$ by Fishers Exact test) and the protective efficacy was 55.2%, 85.1%, and 85.1% for Ty21a-Sso, Ty21a-YBC-Sso, and Ty21a-YBC-Sso+ARA, respectively.

REFERENCES

1. Bryce, J., et al., WHO estimates of the causes of death in children. Lancet, 2005. 365(9465): p. 1147-52.
2. Bardhan, P., et al., Decrease in shigellosis-related deaths without *Shigella* spp.—specific interventions, Asia. Emerging Infectious Diseases, 2010. 16(11): p. 1718-23.
3. Livio, S., et al., *Shigella* Isolates From the Global Enteric Multicenter Study Inform Vaccine Development. Clin Infect Dis, 2014.
4. Scallan, E., et al., Foodborne illness acquired in the United States-major pathogens. Emerg Infect Dis, 2011. 17(1): p. 7-15.
5. Bowen, A., et al., Notes from the Field: Outbreaks of *Shigella sonnei* Infection with Decreased Susceptibility to Azithromycin Among Men Who Have Sex with Men—Chicago and Metropolitan Minneapolis-St. Paul, 2014. MMWR Morb Mortal Wkly Rep, 2015. 64(21): p. 597-8.
6. Howie, R. L., et al., Reduced azithromycin susceptibility in *Shigella sonnei*, United States. Microb Drug Resist, 2010. 16(4): p. 245-8.
7. Sjolund Karlsson, M., et al., Outbreak of infections caused by *Shigella sonnei* with reduced susceptibility to azithromycin in the United States. Antimicrob Agents Chemother, 2013. 57(3): p. 1559-60.
8. Gu, B., et al., Comparison of the prevalence and changing resistance to nalidixic acid and ciprofloxacin of *Shigella* between Europe-America and Asia-Africa from 1998 to 2009. Int J Antimicrob Agents, 2012. 40(1): p. 9-17.
9. Robbins, J. B., C. Chu, and R. Schneerson, Hypothesis for vaccine development: protective immunity to enteric diseases caused by nontyphoidal salmonellae and shigellae may be conferred by serum IgG antibodies to the O-specific polysaccharide of their lipopolysaccharides. Clin Infect Dis, 1992. 15(2): p. 346-61.
10. Kopecko, D. J., et al., Genetic stability of vaccine strain *Salmonella Typhi* Ty21a over 25 years. Int J Med Microbiol, 2009. 299(4): p. 233-46.
11. Levine, M. M., Typhoidfever vaccines, in Vaccines, S. A. Plotkin and W. A. Orenstein, Editors. 1999, W. B. Saunders: Philadelphia. p. 781-814.
12. Levine, M. M., et al., Duration of efficacy of Ty21a, attenuated *Salmonella typhi* live oral vaccine. Vaccine, 1999. 17 Suppl 2: p. S22-7.

13. Wahdan, M. H., et al., A controlled field trial of live *Salmonella typhi* strain Ty21a oral vaccine against typhoid: three-year results. Journal of Infectious Diseases, 1982. 145(3): p. 292-5.
14. Gilman, R. H., et al., Evaluation of a UDP-glucose-4-epimeraseless mutant of *Salmonella typhi* as a liver oral vaccine. J Infect Dis, 1977. 136(6): p. 717-23.
15. Cryz, S. J., Jr., Post-marketing experience with live oral Ty21a vaccine. Lancet, 1993. 341(8836): p. 49-50.
16. Simanjuntak, C. H., et al., Oral immunisation against typhoid fever in Indonesia with Ty21a vaccine. Lancet, 1991. 338(8774): p. 1055-9.
17. Levine, M. M., et al., Development of vaccines and drugs against diarrhea: 11th Nobel Conference, Stockholm, 1985, in 11th Noble Conference, J. Holmgren, A. Lindberg, and R. Möllby, Editors. 1986, Student lilteratur, Lund, Sweden: Stockholm. p. 90-101.
18. Ohtake, S., et al., Room temperature stabilization of oral, live attenuated *Salmonella enterica* serovar *Typhi*-vectored vaccines. Vaccine, 2011. 29(15): p. 2761-71.
19. Dharmasena, M. N., et al., Stable expression of *Shigella sonnei* form I O-polysaccharide genes recombineered into the chromosome of live *Salmonella* oral vaccine vector Ty21a. International Journal of Medical Microbiology, 2013. 303(3): p. 105-13.
20. Pickett, T. E., et al., In vivo characterization of the murine intranasal model for assessing the immunogenicity of attenuated *Salmonella enterica* serovar *Typhi* strains as live mucosal vaccines and as live vectors. Infect Immun, 2000. 68(1): p. 205-13.
21. Lin, J., et al., Comparative analysis of extreme acid survival in *Salmonella typhimurium, Shigella flexneri*, and *Escherichia coli*. Journal of Bacteriology, 1995. 177 (14): p. 4097-104.
22. Gorden, J. and P. L. Small, Acid resistance in enteric bacteria. Infect Immun, 1993. 61(1): p. 364-7.
23. Audia, J. P., C. C. Webb, and J. W. Foster, Breaking through the acid barrier: an orchestrated response to proton stress by enteric bacteria. International Journal of Medical Microbiology, 2001. 291(2): p. 97-106.
24. Foster, J. W., *Salmonella* acid shockproteins are required for the adaptive acid tolerance response. J Bacteriol, 1991. 173(21): p. 6896-902.
25. Foster, J. W., The acid tolerance response of *Salmonella typhimurium* involves transient synthesis of key acid shockproteins. J Bacteriol, 1993. 175(7): p. 1981-7.
26. Foster, J. W., Low pH adaptation and the acid tolerance response of *Salmonella typhimurium*. Crit Rev Microbiol, 1995. 21(4): p. 215-37.
27. Robbe-Saule, V. and F. Norel, The rpoS mutant allele of *Salmonella typhi* Ty2 is identical to that of the live typhoid vaccine Ty21a. FEMS Microbiol Lett, 1999. 170(1): p. 141-3.
28. Germanier, R. and E. Fuer, Isolation and characterization of Gal E mutant Ty21a of *Salmonella typhi*: a candidate strain for a live, oral typhoid vaccine. Journal of Infectious Diseases, 1975. 131(5): p. 553-8.
29. Hone, D. M., A. M. Harris, and M. M. Levine, Adaptive acid tolerance response by *Salmonella typhi* and candidate live oral typhoid vaccine strains. Vaccine, 1994. 12(10): p. 895-8.
30. Kantele, A., et al., Comparison of the human immune response to live oral, killed oral or killed parenteral *Salmonella typhi* TY21A vaccines. Microb Pathog, 1991. 10(2): p. 117-26.
31. Waterman, S. R. and P. L. Small, Identification of the promoter regions and sigma(s)-dependent regulation of the gadA and gadBC genes associated with glutamate-dependent acid resistance in *Shigella flexneri*. FEMS Microbiology Letters, 2003. 225(1): p. 155-60.
32. Bhagwat, A. A. and M. Bhagwat, Comparative analysis of transcriptional regulatory elements of glutamate-dependent acid-resistance systems of *Shigella flexneri* and *Escherichia coli* O157:H7. FEMS Microbiology Letters, 2004. 234(1): p. 139-47.
33. Lin, J., et al., Mechanisms of acid resistance in enterohemorrhagic *Escherichia coli*. Appl Environ Microbiol, 1996. 62(9): p. 3094-100.
34. Brenneman, K. E., et al., Low-pH rescue of acid-sensitive *Salmonella enterica* Serovar *Typhi* Strains by a Rhamnose-regulated arginine decarboxylase system. J Bacteriol, 2013. 195(13): p. 3062-72.
35. De Biase, D. and E. Pennacchietti, Glutamate decarboxylase-dependent acid resistance in orally acquired bacteria: function, distribution and biomedical implications of the gadBC operon. Mol Microbiol, 2012. 86(4): p. 770-86.
36. Merrell, D. S. and A. Camilli, Acid tolerance of gastrointestinal pathogens. Curr Opin Microbiol, 2002. 5(1): p. 51-5.
37. Zhao, B. and W. A. Houry, Acid stress response in enteropathogenic gammaproteobacteria: an aptitude for survival. Biochem Cell Biol, 2010. 88(2): p. 301-14.
38. Hersh, B. M., et al., A glutamate-dependent acid resistance gene in *Escherichia coli*. J Bacteriol, 1996. 178(13): p. 3978-81.
39. Smith, D. K., et al., *Escherichia coli* has two homologous glutamate decarboxylase genes that map to distinct loci. J Bacteriol, 1992. 174(18): p. 5820-6.
40. Lu, P., et al., L-glutamine provides acid resistance for *Escherichia coli* through enzymatic release of ammonia. Cell Res, 2013. 23(5): p. 635-44.
41. Ma, D., et al., Structure and mechanism of a glutamate-GABA antiporter. Nature, 2012. 483(7391): p. 632-6.
42. Kopecko, D. J., O. Washington, and S. B. Formal, Genetic and physical evidence for plasmid control of *Shigella sonnei* form I cell surface antigen. Infect Immun, 1980. 29(1): p. 207-14.
43. Datsenko, K. A. and B. L. Wanner, One-step inactivation of chromosomal genes in *Escherichia coli* K-12 using PCR products. Proc Natl Acad Sci USA, 2000. 97(12): p. 6640-5.
44. Cherepanov, P. P. and W. Wackernagel, Gene disruption in *Escherichia coli*: TcR and KmR cassettes with the option of Flp-catalyzed excision of the antibiotic-resistance determinant. Gene, 1995. 158(1): p. 9-14.
45. Rice, E. W., et al., Rapid glutamate decarboxylase assay for detection of *Escherichia coli*. Appl Environ Microbiol, 1993. 59(12): p. 4347-9.
46. Xu, D. Q., et al., Molecular cloning and characterization of genes for *Shigella sonnei* form I O polysaccharide: proposed biosynthetic pathway and stable expression in a live *salmonella* vaccine vector. Infect Immun, 2002. 70(8): p. 4414-23.
47. Shepherd, J. G., L. Wang, and P. R. Reeves, Comparison of O-antigen gene clusters of *Escherichia coli* (*Shigella*) *sonnei* and *Plesiomonas shigelloides* O17: *sonnei* gained its current plasmid-borne O-antigen genes from *P. shigelloides* in a recent event. Infect Immun, 2000. 68(10): p. 6056-61.
48. Vivotif [package insert-USA]. Crucell Switzerland LTD; September 2013. worldwideweb.fda.gov/downloads/BiologicsBloodVaccines/Vaccines/ApprovedProducts/UCM142807.pdf.
49. Curtiss, III, R., et al., Attenuated live bacteria with increased acid resistance and methods of use thereof. U.S. Patent Publication US2014/0370057 A1, pub. Dec. 18, 2014.
50. Kopecko, D. J., et al., Genetic stability of vaccine strain *Salmonella Typhi* Ty21a over 25 years. Int J Med Microbiol, 2009. 299(4): p. 233-46.

Tables

TABLE I

Bacterial strains and plasmids used in this study

| Strain or plasmid | Description | Reference or source |
|---|---|---|
| Bacterial strains | | |
| *E. coli* NEB5α | cloning | New England Biolabs |
| *Salmonella enterica* serovar Typhi Ty21a | | [14, 48] |
| Ty21a-Sso (wzz–), clone #3-1 (SEQ ID NO: 3) | Ty21a with a chromosomally integrated *S. sonnei* form I O antigen gene cluster at the tviE locus. The first 495 bp of wzz gene is absent. | This study |
| Ty21a-Sso wzz+, clone #9-26 (SEQ ID NO: 4) | Ty21a with a chromosomally integrated *S. sonnei* form I O antigen gene cluster at the tviE locus. Full-length wzz gene and its 100 bp upstream sequence are present. | This study |
| Ty21a-ABC, clone #2-2 (SEQ ID NO: 2) | Ty21a with a chromosomally integrated *S. flexneri* 2a GadA, GadB, and GadC genes under arabinose promoter at the tviE locus | This study |
| Ty21a-YBC, clone #1-28 (SEQ ID NO: 1) | Ty21a with a chromosomally integrated *S. sonnei* YbaS, *S. flexneri* 2a GadB and GadC under arabinose promoter at the tviE locus | This study |
| Ty21a-ABC-Sso, clone #20-25 (SEQ ID NO: 5) | Ty21a with a chromosomally integrated *S. flexneri* 2a GadA, GadB, and GadC genes under arabinose promoter followed by *S. sonnei* form I O antigen gene cluster with full-length wzz at the tviE locus | This study |
| Ty21a-YBC-Sso, clone #34-1 (SEQ ID NO: 6) | Ty21a with a chromosomally integrated *S. sonnei* YbaS, *S. flexneri* 2a GadB, and GadC genes under arabinose promoter followed by *S. sonnei* form I O antigen gene cluster with full-length wzz at the tviE locus | This study |
| *Shigella sonnei* 53G I | Form I (Phase I), virulent isolate | [42] |
| *Shigella sonnei* 53G II | Form II (Phase II), avirulent isolate | [42] |
| Plasmids | | |
| pUC19 | Cloning vector | New England Biolabs |
| pMDTV | Low copy pGB2 vector with inserts of tviD and vexA sequences from Ty21a, separated by FRT-flanked kanamycin resistance gene (KanR) | [19] |
| pKD46 | Temperature sensitive plasmid with bacteriophage λ genes Redα, Redβ, and Redγ expressed under the control of the arabinose-inducible promoter ($P_{ara}$). Used for genetic recombineering. | [43] |
| pCP20 | Temperature sensitive plasmid carrying a constitutively expressed yeast flip recombinase (FLP). Used to remove KanR marker. | [44] |
| pMDTV::Sso O Ag (wzz–) | DNA template for construction of Ty21a-Sso (wzz–) | This study |
| pMDTV::Sso O Ag wzz+ | DNA template for construction of Ty21a-Sso (wzz+) | This study |
| pUC19::AraC-GadABC-KanR-VexA | DNA template for construction of Ty21a-ABC | This study |
| pUC19::AraC-YadC-GadBC-KanR-VexA | DNA template for construction of Ty21a-YBC | This study |
| pTIKV::AraC-YadC-GadBC-Sso O Ag wzz+ | DNA template for construction of Ty21a-ABC-Sso and Ty21a-YBC-Sso | This study |

TABLE II

Characterization of the Ty21a-Sso seedbank

| Assay | Method | Vial 1 | Vial 2 | Ty21a | Ty2 |
|---|---|---|---|---|---|
| Microbiological | API 20 E | *S. typhi* | *S. typhi* | *S. typhi* | *S. typhi* |
| | Galactose fermentation (Colony appearance on Bromothymol Blue agar + 1% galactose) | Blue | Blue | Blue | Yellow |
| Biochemical | Minimal media + cysteine + tryptophan | No growth | No growth | No growth | Growth |
| | Minimal media + cysteine + tryptophan + valine + isoleucine | Growth | Growth | Growth | Growth |
| | Heat stress at 55° C. for 20 min | Sensitive | Sensitive | Sensitive | Resistant |
| | Oxidative stress in 0.3% $H_2O_2$ for 20 min | Sensitive | Sensitive | Sensitive | Resistant |
| | Galactose (1%)-induced bacteriolysis | Sensitive | Sensitive | Sensitive | Resistant |
| Immunological | *Salmonella* group 9,12 O-antigen agglutination | + | + | + | + |
| | Vi antigen agglutination | – | – | – | + |

TABLE II-continued

Characterization of the Ty21a-Sso seedbank

| Assay | Method | Vial 1 | Vial 2 | Ty21a | Ty2 |
|---|---|---|---|---|---|
| | S. sonnei O—Ag Expression (Colony and Western blot) at 200 generations | + | + | − | ND |
| Genetic | 16S rDNA sequence | Identical to Ty21a | Identical to Ty21a | Ty21a | Ty2 |
| | galE DNA sequence | Identical to Ty21a | Identical to Ty21a | Ty21a (T367C; C442Δ) | Ty2 (wild type) |
| | Chromosomally integrated S. sonnei form I O—Ag gene cluster (PCR) | + | + | − | − |

SEQUENCE LISTING

The patent contains a lengthy sequence listing. A copy of the sequence listing is available in electronic form from the USPTO web site (https://seqdata.uspto.gov/?pageRequest=docDetail&DocID=US12409213B2). An electronic copy of the sequence listing will also be available from the USPTO upon request and payment of the fee set forth in 37 CFR 1.19(b)(3).

What is claimed is:

1. A method of treating or reducing the incidence of shigellosis in a human subject comprising oral administration of one or more doses of a vaccine, said vaccine comprising a transgenic Ty21a Salmonella typhi Ty21a, which comprises (i) a heterologous Shigella sonnei O-antigen biosynthetic gene region comprising a wzz gene, wherein the wzz gene comprises a DNA sequence that shares at least 95% sequence identity with the DNA sequence of nucleic acids 4,511,904 to 4,513,010 of SEQ ID NO: 4; and (ii) a heterologous acid resistance biosynthetic gene system comprising one or more YbaS genes; wherein said heterologous Shigella sonnei O-antigen biosynthetic gene region and said heterologous acid resistance biosynthetic gene system are both integrated into the Salmonella typhi Ty21a chromosome, and wherein:
   a. the heterologous Shigella sonnei O-antigen is stably expressed;
   b. the one or more YbaS genes are stably expressed;
   c. said transgenic Salmonella typhi Ty21a is more acid stable at pH 2.5 than Salmonella typhi Ty21a without the integrated acid resistance biosynthetic gene system;
   d. an immune response is elicited against virulent Shigella sonnei challenge; and,
   e. an immune response is elicited against virulent Salmonella typhi challenge.

2. The method of claim 1, wherein the wzz gene comprises the DNA sequence of nucleic acids 4,511,904 to 4,513,010 of SEQ ID NO: 4.

3. The method of claim 1, wherein the heterologous Shigella sonnei O-antigen biosynthetic gene region comprises (i) a DNA sequence that shares at least 95% sequence identity with the DNA sequence of nucleic acids 4,500,076 to 4,513,461 of SEQ ID NO: 4; or (ii) the DNA sequence of nucleic acids 4,500,076 to 4,513,461 of SEQ ID NO: 4.

4. The method of claim 1, wherein the YbaS gene comprises (i) a DNA sequence that shares at least 95% sequence identity with the DNA sequence of nucleic acids 4,503,240 to 4,504,172 of SEQ ID NO: 1, or (ii) the DNA sequence of nucleic acids 4,503,240 to 4,504,172 of SEQ ID NO: 1.

5. The method of claim 1, wherein the Ty21a Salmonella typhi Ty21a further comprises an O-antigen biosynthetic gene region from a bacterial strain selected from the group consisting of: Shigella dysenteriae, Shigella flexneri, Shigella boydii, Escherichia coli, Salmonela enterica serovars, Vibrio cholera serotypes, Enterobacter species, Yersinia species, and Pseudomonas species.

6. The method of claim 1 comprising treating or reducing the incidence of both shigellosis and typhoid fever in the human subject.

7. The method of claim 1, wherein administration of said vaccine to a plurality of human subjects in a human population reduces the incidence of shigellosis in said human population subsequently exposed to pathogenic Shigella sonnei.

8. A method of treating or reducing the incidence of enterotoxogenic E. coli (ETEC) in a human subject comprising oral administration of one or more doses of a vaccine, said vaccine comprising a transgenic Ty21a Salmonella typhi Ty21a comprising (i) a heterologous ETEC antigen biosynthetic gene region, and (ii) a heterologous acid resistance biosynthetic gene system comprising one or more YbaS genes; wherein said ETEC antigen biosynthetic gene region and said acid resistance biosynthetic gene system are both integrated into the Salmonella typhi Ty21a chromosome, and wherein:
   a. the ETEC antigen is stably expressed;
   b. the one or more YbaS genes are stably expressed;
   c. said transgenic Salmonella typhi Ty21a is more acid stable at pH 2.5 than Salmonella typhi Ty21a without the integrated acid resistance biosynthetic gene system;
   d. an immune response is elicited against virulent Enterotoxogenic E. coli challenge; and
   e. an immune response is elicited against virulent Salmonella typhi challenge.

9. The method of claim 8, wherein the YbaS gene comprises (i) a DNA sequence that shares at least 95% sequence identity with the DNA sequence of nucleic acids 4,503,240 to 4,504,172 of SEQ ID NO: 1, or (ii) the DNA sequence of nucleic acids 4,503,240 to 4,504,172 of SEQ ID NO: 1 or a complementary sequence thereof.

10. The method of claim 8 comprising treating or reducing the incidence of both ETEC and typhoid fever in the human subject.

11. The method of claim 8, wherein administration of said vaccine to a plurality of human subjects in a human population reduces the incidence of ETEC in said human population subsequently exposed to ETEC.

* * * * *